United States Patent
Nguyen et al.

(10) Patent No.: US 9,060,773 B2
(45) Date of Patent: Jun. 23, 2015

(54) OCCLUSIVE IMPLANT DELIVERY DEVICES AND ASSOCIATED METHODS

(75) Inventors: Hoa D. Nguyen, San Jose, CA (US); Michael S. Mirizzi, San Jose, CA (US); Thomas C. Pham, San Jose, CA (US)

(73) Assignee: Covidien LP, Mansfield, MA (US)

( * ) Notice: Subject to any disclaimer, the term of this patent is extended or adjusted under 35 U.S.C. 154(b) by 521 days.

(21) Appl. No.: 13/328,357

(22) Filed: Dec. 16, 2011

(65) Prior Publication Data

US 2013/0152941 A1 Jun. 20, 2013

(51) Int. Cl.
*A61F 6/06* (2006.01)
*A61B 17/12* (2006.01)
*A61F 2/80* (2006.01)

(52) U.S. Cl.
CPC ..... *A61B 17/12022* (2013.01); *A61B 17/12099* (2013.01); *A61B 2017/1205* (2013.01); *A61F 2/80* (2013.01); *A61F 2002/805* (2013.01)

(58) Field of Classification Search
USPC .................................. 128/830, 831
See application file for complete search history.

(56) References Cited

U.S. PATENT DOCUMENTS

| | | | |
|---|---|---|---|
| 3,805,767 A | 4/1974 | Erb | |
| 4,109,654 A | 8/1978 | Bolduc et al. | |
| 5,108,420 A | 4/1992 | Marks | |
| 5,342,394 A | 8/1994 | Matsuno et al. | |
| 5,389,100 A | 2/1995 | Bacich et al. | |
| 5,601,600 A | 2/1997 | Ton | |
| 6,709,667 B1 | 3/2004 | Lowe et al. | |
| 7,445,613 B2 | 11/2008 | Hommann | |
| 7,591,268 B2 | 9/2009 | Lowe et al. | |
| 7,815,661 B2 * | 10/2010 | Mirizzi et al. | 606/213 |
| 2003/0015203 A1 | 1/2003 | Makower et al. | |
| 2005/0222605 A1 | 10/2005 | Greenhalgh et al. | |
| 2005/0274384 A1 | 12/2005 | Tran et al. | |
| 2005/0288551 A1 | 12/2005 | Callister et al. | |
| 2006/0229669 A1 | 10/2006 | Mirizzi et al. | |
| 2007/0227544 A1 | 10/2007 | Swann et al. | |
| 2007/0244439 A1 | 10/2007 | Mujwid et al. | |
| 2010/0076379 A1 | 3/2010 | Matusch | |
| 2010/0106090 A1 | 4/2010 | Matusch | |
| 2010/0168514 A1 | 7/2010 | Callister et al. | |
| 2011/0061660 A1 | 3/2011 | Cruzada et al. | |
| 2011/0094519 A1 | 4/2011 | Gopal et al. | |

FOREIGN PATENT DOCUMENTS

| | | |
|---|---|---|
| JP | 2008-528128 | 7/2008 |
| WO | WO 2011/089436 A2 | 7/2011 |

OTHER PUBLICATIONS

Patent Examination Report dated Mar. 9, 2013 in relation to Australian application No. 2012258347.
Foreign Office Action on related Japanese Application No. 2012-272758 dated Nov. 11, 2013.

* cited by examiner

*Primary Examiner* — Victoria J Hicks
(74) *Attorney, Agent, or Firm* — Thomas M. Johnston, Esq.

(57) ABSTRACT

The various embodiments simplify the delivery of an occlusive implant to a hollow anatomical structure, such as a fallopian tube. For example, the delivery devices don't need to be retracted manually to deploy the implant. When the devices are activated, stored energy or a powered drive member induces movement of the various components. The operator need only position the distal ends of the devices at the treatment site and then commence deployment by, for example, flipping a switch or changing the position of an activation button. The present embodiments thus increase the efficacy of occlusion procedures by reducing the likelihood of operator error.

13 Claims, 18 Drawing Sheets

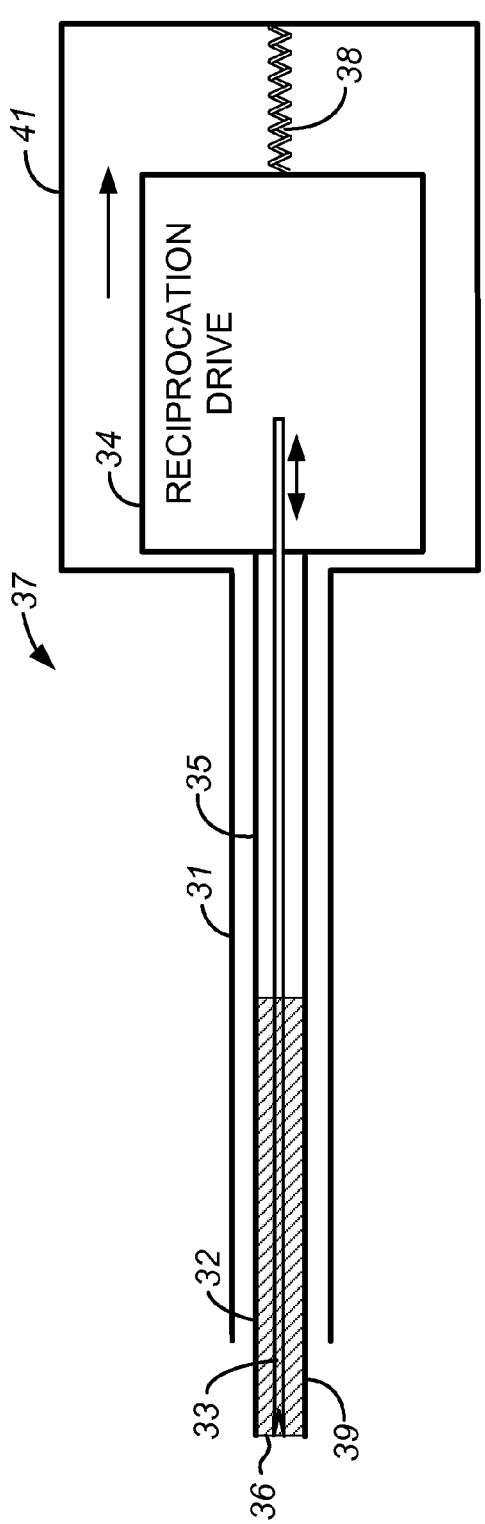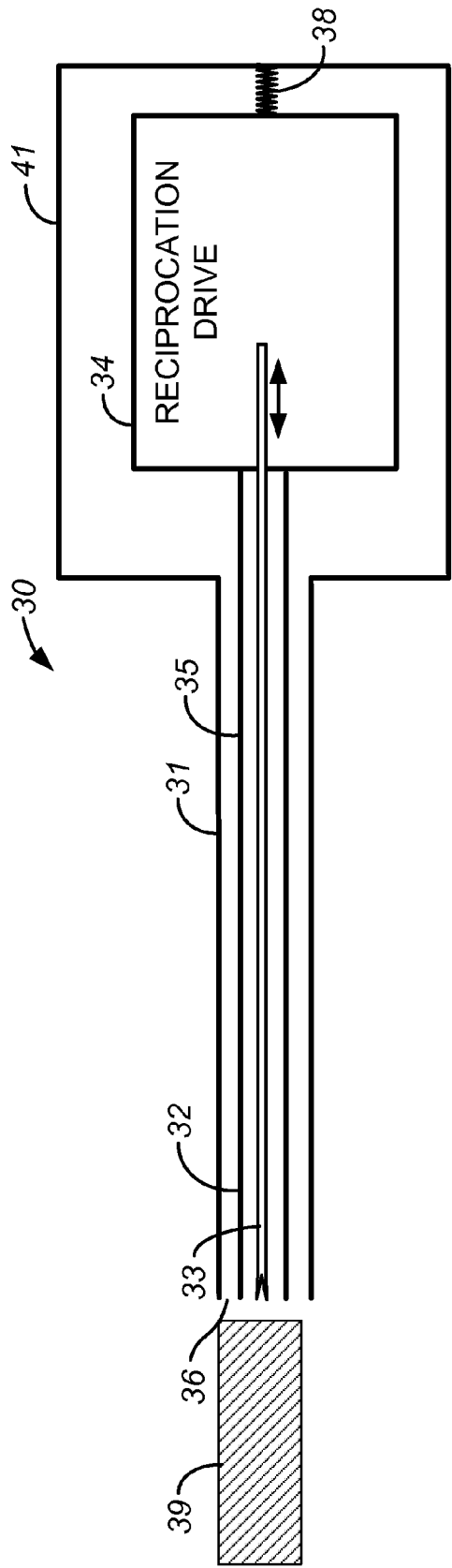

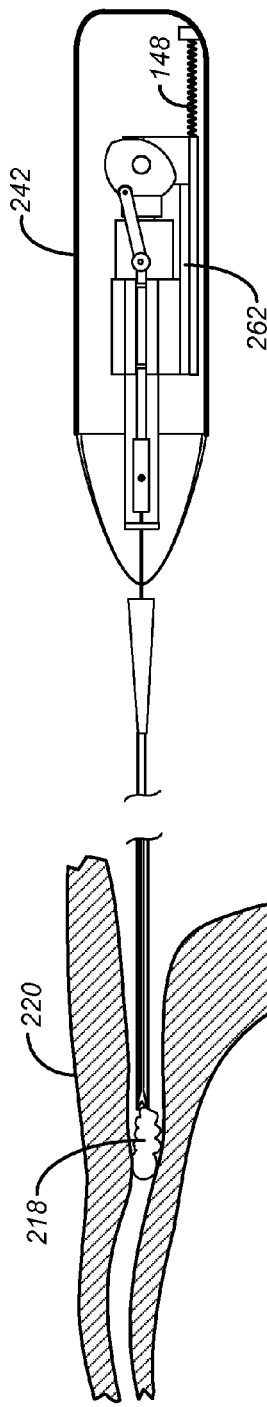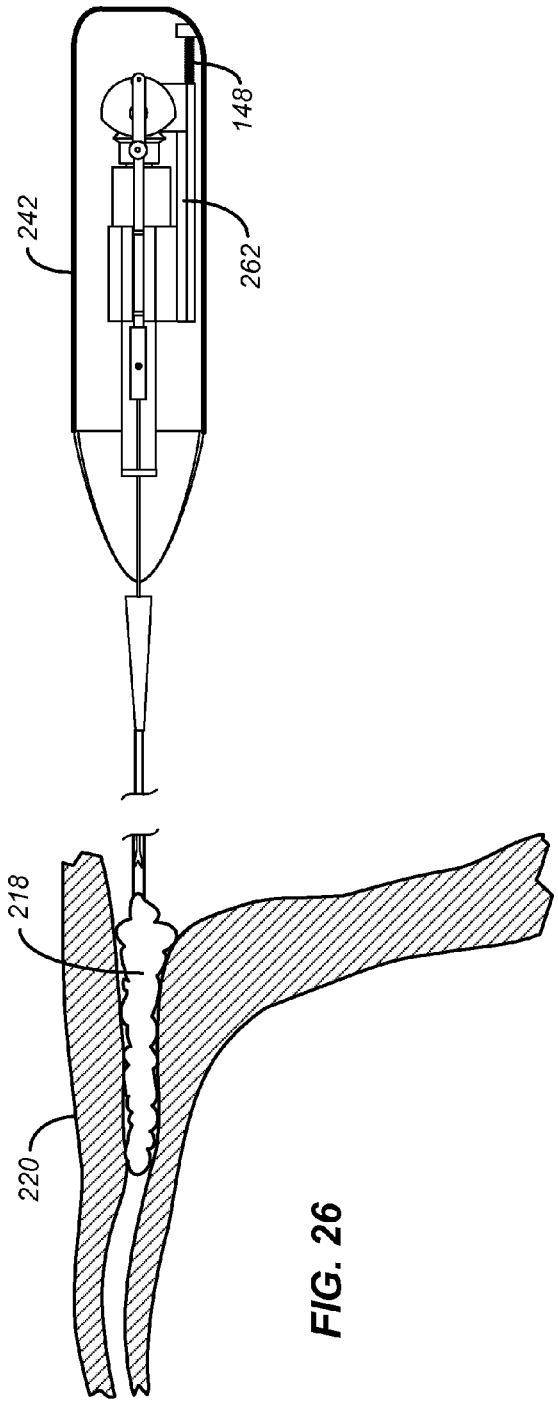
FIG. 25
FIG. 26

OCCLUSIVE IMPLANT DELIVERY DEVICES AND ASSOCIATED METHODS

TECHNICAL FIELD

The present invention relates to apparatus and methods for delivering occlusive implants into hollow anatomical structures.

BACKGROUND

Numerous devices and methods for contraception are currently in use. Examples include condoms, diaphragms, intrauterine devices (IUDs), fallopian tube ligation, vasectomy, etc. Each of these devices and methods, however, has drawbacks. For example, condoms and diaphragms are not 100% effective. IUDs have been associated with serious infectious complications. Fallopian tube ligation and vasectomy are surgical procedures, and therefore bear all of the attendant risks of surgery.

Another form of contraception involves placing occlusive implants within the fallopian tubes through a transcervical procedure. Transcervical procedures may be preferred over surgical procedures due to the decreased risk of complications. However, these procedures present challenges. In particular, the inside diameter of a fallopian tube is small, on the order of 0.8-1.2 mm. Further, the cross-sectional shape of the internal surface of a fallopian tube is not smooth. Rather, it has a scalloped appearance with a plurality of adjoining lobes. It can thus be difficult to completely occlude a fallopian tube.

SUMMARY

The various embodiments of the present occlusive implant delivery devices and associated methods have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

One of the present embodiments comprises a method. The method comprises, with a delivery system including an outer sheath, an inner sheath slidably received within the outer sheath, an elongate pusher member received within the inner sheath, and the occlusive implant received within the inner sheath, longitudinally reciprocating the pusher member within the inner sheath to segmentally expel the implant from a distal end of the inner sheath, while simultaneously retracting the inner sheath proximally within the outer sheath.

Another of the present embodiments comprises apparatus for delivering an occlusive implant to a treatment site. The apparatus comprises a delivery system including an outer sheath having a distal tip sized and configured for transcervical insertion, an inner sheath slidably received within the outer sheath and having a distal tip sized and configured for transcervical insertion, and an elongate pusher member received within the inner sheath. The inner sheath has a distalmost first position in which the distal tip of the inner sheath is located distally of the distal tip of the outer sheath, and is retractable to a second position in which the distal tip of the inner sheath is closer to the distal tip of the outer sheath. The apparatus further comprises an occlusive implant sized and configured for insertion into a fallopian tube, and slidably received within the inner sheath about the pusher member. The apparatus further comprises a reciprocation drive configured to reciprocate the pusher member longitudinally within the inner sheath as the inner sheath retracts proximally toward the distal tip of the outer sheath.

Another of the present embodiments comprises apparatus for delivering an occlusive implant to a hollow anatomical structure. The apparatus comprises a housing defining a body of the apparatus. The apparatus further comprises a slidable base within the housing. The slidable base is configured to move longitudinally with respect to the housing. The apparatus further comprises a retractable sheath extending distally from the slidable base. The retractable sheath is movable with the slidable base. The apparatus further comprises a reciprocating pushing member extending at least partially through a lumen of the retractable sheath. The occlusive implant occupies a space around the pushing member and within the retractable sheath. The apparatus further comprises a flywheel coupled to the base and capable of rotating with respect to the base about an axis perpendicular to the longitudinal axis of the apparatus. The apparatus further comprises a link rod coupled at a distal end to the base and to the reciprocating pushing member and at a proximal end to the flywheel at a location spaced from a center of rotation of the flywheel, such that rotation of the flywheel induces reciprocating longitudinal motion of the pushing member through the link rod.

Another of the present embodiments comprises a method of delivering an occlusive implant to a treatment site in a hollow anatomical structure. The method comprises accessing the treatment site using an apparatus for delivering the occlusive implant. The apparatus comprises a housing defining a body of the apparatus. The apparatus further comprises a slidable base within the housing. The slidable base is capable of moving longitudinally with respect to the housing. The apparatus further comprises a retractable sheath extending distally from the slidable base. The retractable sheath is movable with the slidable base. The apparatus further comprises a reciprocating pushing member extending at least partially through a lumen of the retractable sheath. The occlusive implant occupies a space around the pushing member and within the retractable sheath. The method further comprises positioning a distal end of the retractable sheath at the treatment site. The method further comprises releasing a brake on the apparatus, thereby causing the slidable base to slide proximally within the housing in discrete increments thereby causing the retractable sheath to move proximally, while at the same time causing the pushing member to reciprocate within the retractable sheath lumen to incrementally expel the occlusive implant from the retractable sheath as the retractable sheath moves proximally.

Another of the present embodiments comprises apparatus for delivering an occlusive implant to a hollow anatomical structure. The apparatus comprises a housing defining a body of the apparatus. The apparatus further comprises a slidable base within the housing. The slidable base is configured to move longitudinally with respect to the housing. The apparatus further comprises a retractable sheath extending distally from the slidable base. The retractable sheath is movable with the slidable base. The apparatus further comprises a reciprocating pushing member extending at least partially through a lumen of the retractable sheath. The occlusive implant occupies a space around the pushing member and within the retractable sheath. The apparatus further comprises a flywheel coupled to the base and capable of rotating with respect to the base about an axis perpendicular to the longitudinal axis of the apparatus. The apparatus further comprises a reciprocating piston coupled to a proximal end of the pushing member. The apparatus further comprises a link rod coupled at a distal end to the piston and at a proximal end to the flywheel at a location spaced from a center of rotation of the flywheel, such that rotation of the flywheel induces reciprocating longitudinal motion of the piston, which in turn induces reciprocating longitudinal motion of the pushing member within the retractable sheath.

Another of the present embodiments comprises a method of delivering an occlusive implant to a treatment site in a hollow anatomical structure. The method comprises accessing the treatment site using an apparatus for delivering the occlusive implant. The apparatus comprises a housing defining a body of the apparatus. The apparatus further comprises a slidable base within the housing. The slidable base is capable of moving longitudinally with respect to the housing. The apparatus further comprises a retractable sheath extending distally from the slidable base. The retractable sheath is movable with the slidable base. The apparatus further comprises a reciprocating pushing member extending at least partially through a lumen of the retractable sheath. The occlusive implant occupies a space around the pushing member and within the retractable sheath. The method further comprises positioning a distal end of the retractable sheath at the treatment site. The method further comprises inducing reciprocation of the pushing member within the retractable sheath lumen to thereby begin expelling the occlusive implant from the retractable sheath at a first implant delivery rate. The method further comprises a distal tip of the retractable sheath encountering back pressure from contact with an expelled portion of the occlusive implant. The method further comprises, in response to the back pressure, the retractable sheath retracting.

BRIEF DESCRIPTION OF THE DRAWINGS

The various embodiments of the present occlusive implant delivery devices and associated methods now will be discussed in detail with an emphasis on highlighting the advantageous features. These embodiments depict the novel and non-obvious occlusive implant delivery devices and associated methods shown in the accompanying drawings, which are for illustrative purposes only. These drawings include the following figures, in which like numerals indicate like parts:

FIGS. 2A and 2B are schematic side views of another embodiment of the present occlusive implant delivery devices;

FIG. 4A is a detail view of the portion of FIG. 4 indicated by the area 4A-4A;

FIGS. 25 and 26 are side elevation views of the device of FIG. 21 at successive stages of a procedure for delivering an implant;

DETAILED DESCRIPTION

Figure 1A:
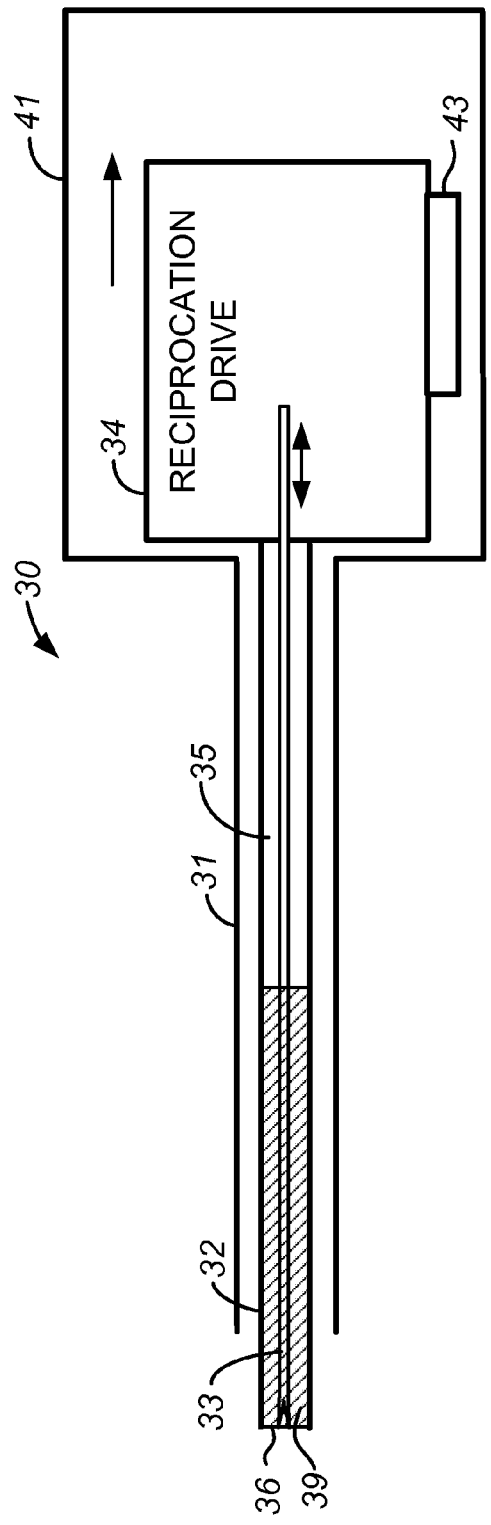
FIGS. 1A and 1B are schematic side views of one embodiment of the present occlusive implant delivery devices.

The following detailed description describes the present embodiments with reference to the drawings. In the drawings, reference numbers label elements of the present embodiments. These reference numbers are reproduced below in connection with the discussion of the corresponding drawing features.

The embodiments of the present occlusive implant delivery devices and associated methods are described below with reference to the figures. These figures, and their written descriptions, indicate that certain components of the apparatus are formed integrally, and certain other components are formed as separate pieces. Components shown and described herein as being formed integrally may in alternative embodiments be formed as separate pieces. Components shown and described herein as being formed as separate pieces may in alternative embodiments be formed integrally. Further, as used herein the term integral describes a single unitary piece.

Directional terms used herein, such as proximal, distal, upper, lower, clockwise, counterclockwise, etc., are used with reference to the configurations shown in the figures. For example, a component that is described as rotating clockwise when viewed from the perspectives shown in the figures may be said to rotate counterclockwise when viewed from the opposite perspective. Furthermore, the present embodiments may be modified by altering or reversing the positions or directions of movement of various components. Accordingly, directional terms used herein should not be interpreted as limiting.

One application for which the present embodiments are well suited is permanent occlusion of fallopian tubes through a transcervical procedure. The present embodiments will thus be described with reference to such a procedure. However, the present embodiments may also be used in any procedure for delivering an occlusive implant to a treatment site in any hollow anatomical structure (HAS). Accordingly, any descriptions herein that relate to occluding fallopian tubes through a transcervical procedure should not be interpreted as limiting the scope of the claims.

Certain of the present embodiments combine reciprocal motion with retraction. Certain others of the present embodiments combine reciprocal motion with incremental retraction. Still certain others of the present embodiments combine reciprocal motion with retraction in response to back pressure.

Certain of the present embodiments comprise a reciprocating drive that retracts while reciprocating. Certain others of the present embodiments comprise a reciprocating drive that incrementally retracts during reciprocation. Still certain others of the present embodiments comprise a reciprocating drive that retracts in response to back pressure during reciprocation.

Figure 1B:
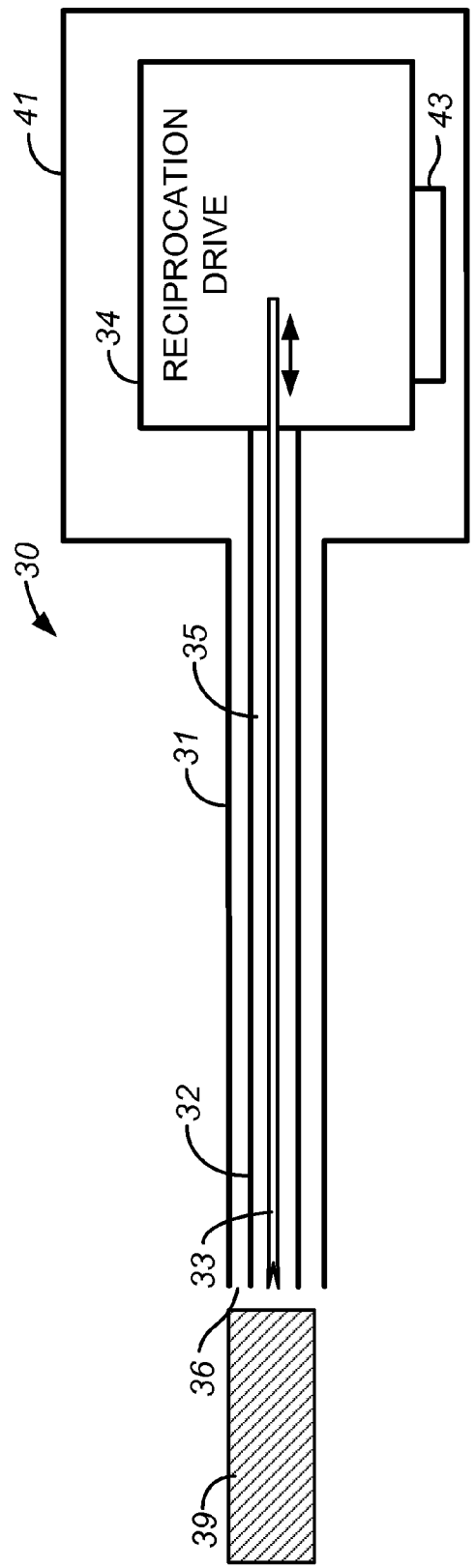

FIGS. 1A and 1B illustrate, schematically, one embodiment of the present occlusive implant delivery devices. This embodiment combines reciprocal motion with retraction, which may be incremental, and may be used to perform methods of delivering an implant to a hollow anatomical structure ("HAS") such as a fallopian tube, including but not limited to the methods of FIGS. 16-19, as described below. FIG. 1A illustrates one embodiment of the device 30 in a start configuration, or distal or distalmost position, while FIG. 1B illustrates the device 30 in an end configuration, or proximal or proximalmost position.

The device 30 comprises a housing 41, a first sheath 31 fixed to a distal end of the housing 41 at a proximal end of the first sheath 31, a second sheath 32 slidably received within the first sheath 31 and fixed to a distal end of a reciprocation drive 34 at a proximal end of the second sheath 32, and a pushing member 33 (e.g. a pushrod) received within the second sheath 32 and drivingly fixed to the reciprocation drive 34 at a proximal end of the pushing member 33. The reciprocation drive 34 can therefore axially reciprocate the pushing member 33 within the second sheath 32 over a predetermined range of reciprocation relative to the second sheath 32 and the reciprocation drive 34. The reciprocation drive 34, second sheath 32, and pushing member 33 are axially retractable together within and/or relative to the first sheath 31 and housing 41, under the influence or guidance of a retraction drive 43, which can connect the reciprocation drive 43 to the housing 41.

The first and second sheaths 31, 32 preferably do not reciprocate. During operation of the device 30, the second sheath 32 retracts proximally within the first sheath 31 due to action of the retraction drive 43 as the pushing member 33 reciprocates within the second sheath 32 due to action of the reciprocation drive 34. The action of the retraction drive 43 induces retraction of the second sheath 32, the (reciprocating) pushing member 33 and the reciprocation drive 34 toward, to or beyond the retracted configuration of the second sheath 32, the pushing member 33 and the reciprocation drive 34 shown in FIG. 1B. The retraction may be incremental or continuous. While the drives 34, 43 are shown as separate components in FIGS. 1A and 1B, the retraction drive 43 may comprise one or more components of the reciprocation drive 34, and vice versa. The reciprocation drive 34 and the retraction drive 43 may be mechanically linked so that activating one of them activates the other. The reciprocation drive 34 and the retraction drive 43 may be contained within the housing 41.

An occlusive implant 39 is positioned in a space or lumen 35 of the second sheath 32, adjacent to and/or surrounding the pushing member 33. Reciprocating movement of the pushing member 33 within the second sheath 32 forces the implant 39 incrementally (e.g. with successive distal strokes of the pushing member 33) out a distal end 36 of the second sheath 32, as the second sheath 32 retracts into the first sheath 31. When the sheaths 31, 32 are positioned within a hollow anatomical structure (not shown in FIGS. 1A-1B), such as a fallopian tube, the device 30 delivers the implant 39 into the HAS from the distal end 36 of the second sheath 32.

The pushing member 33 can have a distal tip (and/or other structures) that are configured to engage the implant 39 in a unidirectional (e.g. distal-only) manner. Accordingly, as the pushing member 33 reciprocates within the second sheath 32, the pushing member 33 can engage and urge the implant 39 along and out of the second sheath 32 substantially only when the pushing member 33 advances distally relative to the second sheath 32, during the distal stroke of the member's reciprocation. As the pushing member 33 retracts proximally, during the proximal reciprocation stroke, the pushing member 33 preferably does not substantially engage the implant 39 or urge the implant proximally. Thus the pushing member 33 can move proximally relative to the implant 39 and second sheath 32 during the proximal stroke, substantially without pulling the implant 39 proximally. When the pushing member 33 completes the proximal stroke and begins another distal stroke, the member 33 can engage the implant 39 again, at location(s) along the implant 39 that is/are proximal of the location(s) where the member 33 engaged the implant 39 on the previous distal stroke, enabling the pushing member 33 to push the implant 39 still further distally as the member makes the next distal stroke. Over a sufficient number of reciprocation cycles, the pushing member 33 urges the implant 39 in such a "ratcheting" fashion distally until the implant 39 exits the second sheath 32.

Within the second sheath 32, the implant 39 can have a radially compacted and longitudinally elongated configuration, but upon expulsion from the second sheath 32, the implant 39 can self-expand radially to embody a radially expanded and longitudinally shortened configuration, as illustrated in a comparison of FIGS. 1A and 1B. Retraction of the second sheath 32, which retraction may be incremental, coupled with reciprocating movement of the pushing member 33 allows the implant 39 to be expelled at a desired rate over a desired length of the HAS. The illustrated device 30 is particularly well suited for placing an occlusive implant within a fallopian tube, but other applications are contemplated. Examples of structure for implementing the embodiment of FIGS. 1A and 1B are described below.

The retraction drive 43 may be active or passive. An active retraction drive actively causes the retraction of the retracted components, for example, via a mechanism that retracts the components in a predetermined fashion. Such active retraction may be incremental or continuous. A passive retraction drive allows, or guides or regulates the retraction of the retracted components in response to an external influence. One such influence may be back pressure acting on the distal tip of the second sheath 32, and/or the implant 39 or pushrod 33. One example of an active retraction drive is described below, incorporated in the device 40 of FIGS. 3-19, 27 and 28. One example of a passive retraction drive includes a biasing member 38, as described below with reference to FIGS. 2A and 2B. Another example of a passive retraction drive is described below, incorporated in the device 240 of FIGS. 15-28.

FIGS. 2A and 2B illustrate, schematically, another embodiment of the present occlusive implant delivery devices, which can be similar to the embodiment of FIGS. 1A and 1B in structure, function and method of use, except as further described herein. This embodiment combines reciprocal motion with passive retraction in response to back pressure, and may be used to perform methods of delivering an implant to an HAS such as a fallopian tube, including but not limited to the methods of FIGS. 16-19 and 25-26, as described below. The device 37 comprises the first sheath 31, the second sheath 32 received within the first sheath 31, the pushing member 33 received within the second sheath 32, the reciprocation drive 34, the implant 39 located in the lumen 35 of the second sheath 32, and the housing 41. These components can be arranged as depicted and described with respect to FIGS. 1A and 1B. The device 37 further comprises a passive retraction drive comprising a biasing member 38 (which may comprise a linear biasing member, such as a spring).

As in the previous embodiment, when the device 37 is activated the reciprocation drive 34 induces reciprocal motion of the pushing member 33 within the second sheath 32 over the predetermined range of motion relative to the second sheath. The first and second sheaths 31, 32 do not reciprocate. However, unlike the embodiment of FIGS. 1A and 1B, the retraction drive does not actively induce retraction of the second sheath 32, the pushing member 33 or the reciprocation drive 34. Rather, the biasing member 38 biases the second sheath 32, the pushing member 33, and the reciprocation drive 34 in the distal direction, and allows, guides and/or regulates the proximal retraction of these components in response to back pressure exerted thereon.

Reciprocating movement of the pushing member 33 within the second sheath 32 forces the implant 39 out the distal end 36 of the second sheath 32 and into the space within the HAS (not shown), such as a fallopian tube, as shown in FIG. 2B. As the implant is expelled, back pressure builds on the implant 39, the pushing member 33 and/or the distal end 36 of the second sheath 32. This back pressure urges the second sheath 32, the pushing member 33, and the reciprocation drive 34 in the proximal direction against the force of the biasing member 38. Therefore, these components will retract only when the back pressure exceeds the distally-directed force exerted by the biasing member 38, resulting in passive retraction. Passive retraction of the second sheath 32 in response to back pressure coupled with reciprocating movement of the pushing member 33 allows the implant to be delivered into an HAS at a desired or substantially uniform packing density over a desired length of the HAS. The achievement of a desired or substantially uniform packing density is discussed in further detail below. The illustrated device 37 is particularly well suited for placing an occlusive implant within a fallopian tube, but other applications are contemplated. FIGS. 15-28 below illustrate a device 240 employing a passive retraction drive. The device 240 can be similar to the device 37 of FIGS. 2A and 2B, except as further described below.

FIGS. 3-19, 27 and 28 illustrate another embodiment of the present occlusive implant delivery devices and associated methods. This embodiment combines reciprocal motion with active, incremental retraction, and may be used to perform methods of delivering an implant to an HAS such as a fallopian tube, including but not limited to the methods of FIGS. 16-19, as described below. The embodiment of FIGS. 3-19, 27 and 28 can be generally similar in structure and function to the embodiment of FIGS. 1A and 1B, except as further described herein. For example, the stationary sheath 198, retractable sheath 194, pushing member 202, occlusive implant 218 and housing 42 of the delivery device 40 of FIGS. 3-19, 27 and 28 can be similar in structure and function to the first sheath 31, second sheath 32, pushing member 33, occlusive implant 39 and housing 41, respectively, of the delivery device 30 of FIGS. 1A and 1B; and vice versa. In the device 40 of FIGS. 3-19, 27 and 28, the torsion spring 86 and the components forming a drivetrain from the torsion spring 86 to the pushing member 202 collectively form a reciprocation drive which can be employed as the reciprocation drive 34 in the device 30 of FIGS. 1A-1B (or in the device 30 of FIGS. 2A-2B, or in the device 240 of FIGS. 15-28). In the device 40 of FIGS. 3-19, 27 and 28, the linear biasing members 148 and the components (rails 56, rails 64, ratchet teeth 52, pawl 150, etc.) that direct the retraction of the retractable sheath 194, pushing member 202, etc., collectively form a retraction drive which can be employed as the retraction drive 43 in the device 30 of FIGS. 1A-1B.

Figure 3:
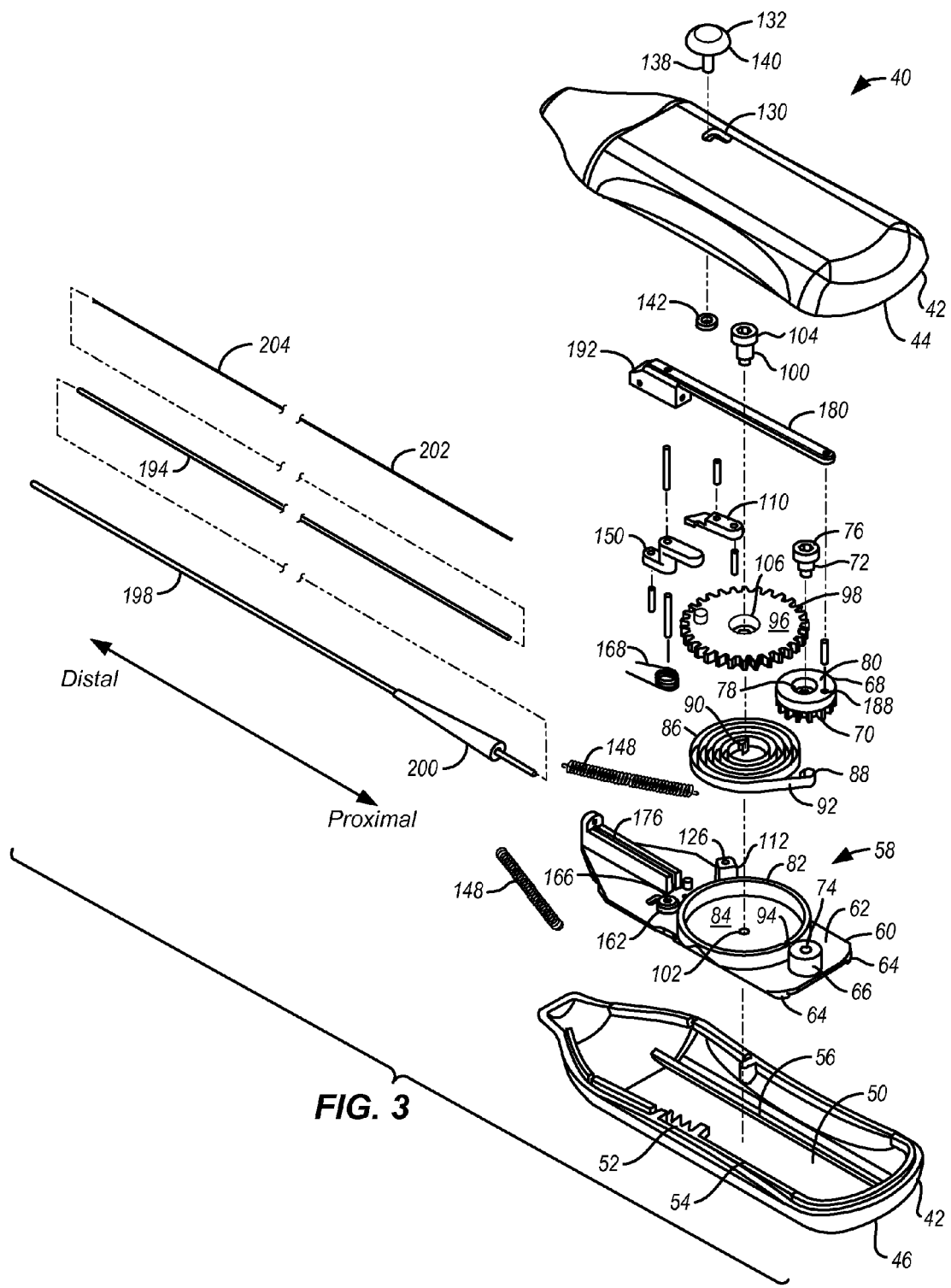
FIG. 3 is an exploded perspective view of another embodiment of the present occlusive implant delivery devices.
Figure 4:
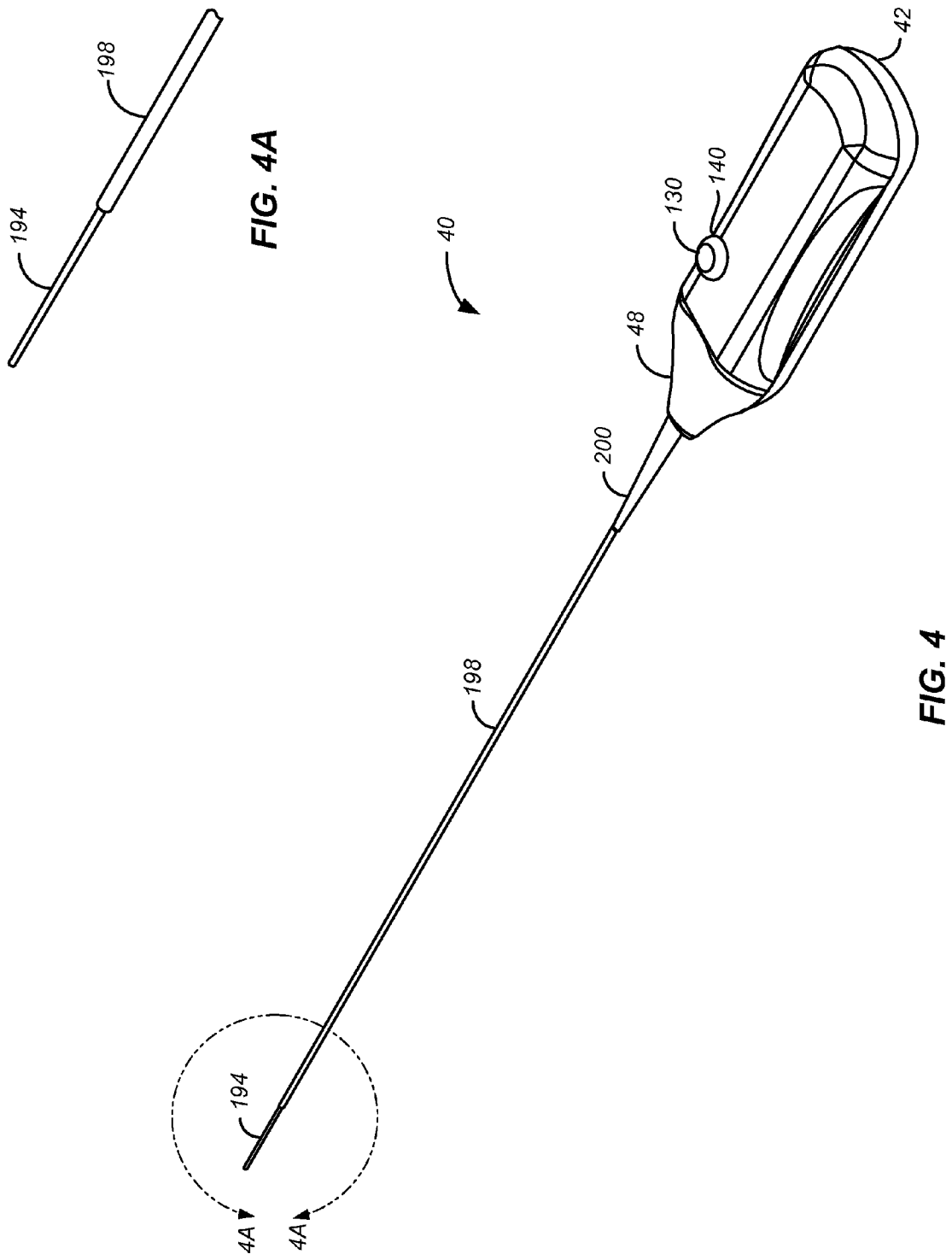
FIG. 4 is an assembled perspective view of the device of FIG. 3.
Figure 5:
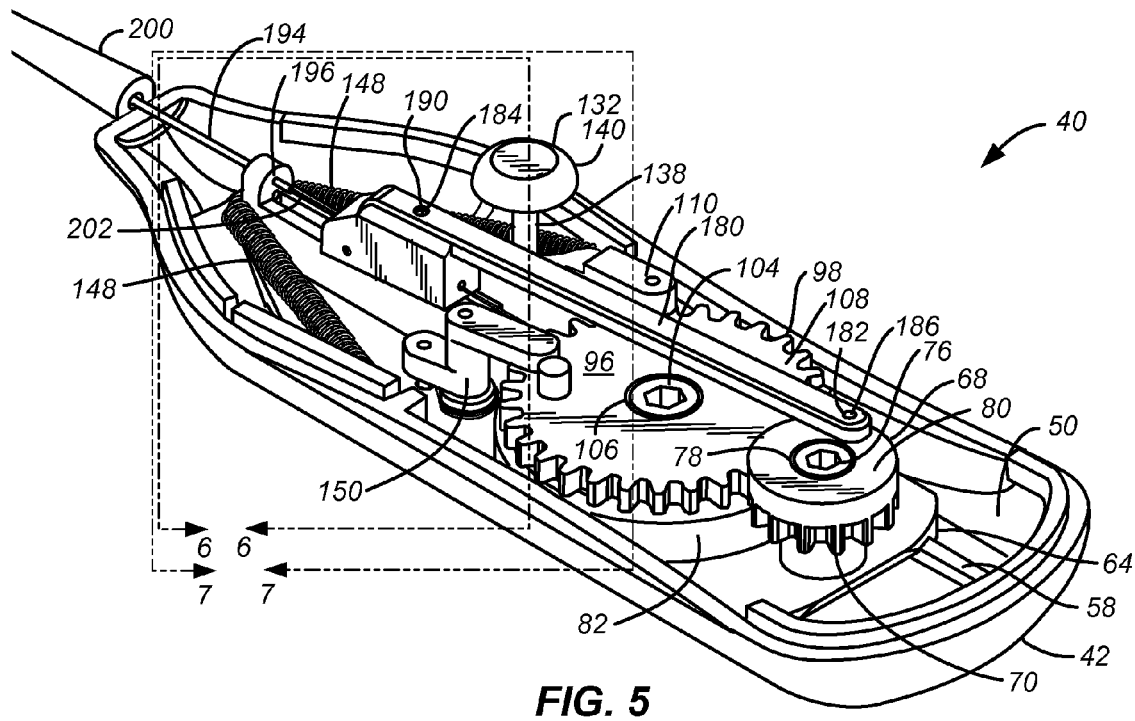
FIG. 5 is a perspective view of the device of FIG. 4 with one portion of the housing removed.

With reference to FIGS. 3-5, the illustrated delivery device 40 includes a housing 42 defining a body of the apparatus. As shown in FIG. 3, the housing 42 includes first and second portions 44, 46 that may be secured to one another in any suitable fashion, such as a snap fit, adhesive, welding, etc. The housing 42 may be of a suitable size and shape to be comfortably held by an operator with one hand. With reference to FIG. 4, in the illustrated embodiment the housing 42 is substantially rectangular in plan view, with rounded corners and an inwardly tapering distal portion 48. However, the housing 42 can have any shape. The housing 42 may be constructed of any suitable material, such as an injection molded plastic.

With reference to FIGS. 3 and 5, the housing 42 includes an interior cavity 50 that receives and retains a plurality of components that are described in further detail below. The second portion 46 includes a plurality of ratchet teeth 52 (FIG. 3) that extend along the inside of a first long edge 54, facing into the cavity 50. In the illustrated embodiment, four ratchet teeth 52 are shown, but any number could be provided. The functionality of the ratchet teeth 52 is described in detail below. The second portion 46 further includes a pair of spaced rails 56 that extend longitudinally. Only one rail 56 is visible in FIG. 3. The functionality of the rails 56 is described below.

With reference to FIGS. 3 and 5, the cavity 50 receives a base 58, which is configured to move within the cavity 50 along a longitudinal axis of the device 40. With reference to FIG. 3, the base 58 includes a planar portion 60 and a plurality of structures that protrude from a first face 62 thereof. A second face (not shown), opposite the first face 62, includes a pair of spaced rails 64 that extend longitudinally. A width between inside edges of the rails 64 is slightly greater than a width between outside edges of the rails 56 on the second portion 46 of the housing 42. The two pairs of rails 56, 64 thus engage one another, as shown in FIG. 5, to limit lateral movement of the base 58 with respect to the housing 42, and to guide longitudinal motion of the base 58.

With reference to FIG. 3, near a proximal end, a hollow cylindrical post 66 extends from the first face 62. With reference to FIGS. 3 and 5, the post 66 receives a flywheel 68 having a plurality of flywheel teeth 70. As illustrated, a threaded male fastener 72 cooperates with a threaded aperture 74 in the post 66 (FIG. 3) to rotatably secure the flywheel 68 to the post 66. A head 76 of the threaded male fastener 72 is countersunk in a recess 78 in the flywheel 68 so that no portion of the threaded male fastener 72 extends above a surface 80 of the flywheel 68. Other types of fasteners may be used to secure the flywheel 68 to the post 66, and the illustrated threaded male fastener 72 and threaded aperture 74 should not be interpreted as limiting the scope of the present disclosure or claims.

Distally of the post 66, a circular ring 82 extends from the first face 62, defining a recess 84 (FIG. 3). The recess 84 receives a torsion spring 86. Opposite ends of the torsion spring 86 include crimps 88, 90. The crimp 88 at a first end is positioned outside the ring 82 in the assembled device 40, with a portion 92 adjacent the crimp passing through an opening 94 in the ring 82. The opening 94 is narrow enough that the crimp 88 cannot pass through it. The ring 82 thus prevents movement of the first end of the torsion spring 86 when the torsion spring 86 is wound in a clockwise direction, as further detailed below.

With continued reference to FIGS. 3 and 5, a gear wheel 96 having a plurality of gear teeth 98 is positioned in facing engagement with the ring 82 and concentric therewith. The gear wheel 96 includes a protrusion (not shown) on a surface facing the torsion spring 86. The protrusion engages the crimp 90 at a second end of the torsion spring 86. Since the crimp 88 at the first end of the torsion spring 86 is held in position by the ring 82, clockwise rotation of the gear wheel 96 winds up the torsion spring 86, storing potential energy therein. When the wound up gear wheel 96 is released, the stored energy is released and the gear wheel 96 rotates in the counterclockwise direction, as described in further detail below. The directions of winding and unwinding for the torsion spring 86 may be reversed in alternative embodiments.

With reference to FIG. 5, the gear teeth 98 engage the flywheel teeth 70, such that rotation of either of the gear wheel 96 and the flywheel 68 induces rotation of the other, as described in detail below. As illustrated, a threaded male fastener 100 cooperates with a threaded aperture 102 in the planar portion 60 of the base 58 (FIG. 3) to rotatably secure the gear wheel 96 to the base 58. A head 104 of the threaded male fastener 100 is countersunk in a recess 106 in the gear wheel 96 so that no portion of the threaded male fastener 100 extends above a surface 108 (FIG. 5) of the gear wheel 96. Other types of fasteners may be used to secure the gear wheel 96 to the base 58, and the illustrated threaded male fastener 100 and threaded aperture 102 should not be interpreted as limiting the scope of the claims herein.

Figure 9:
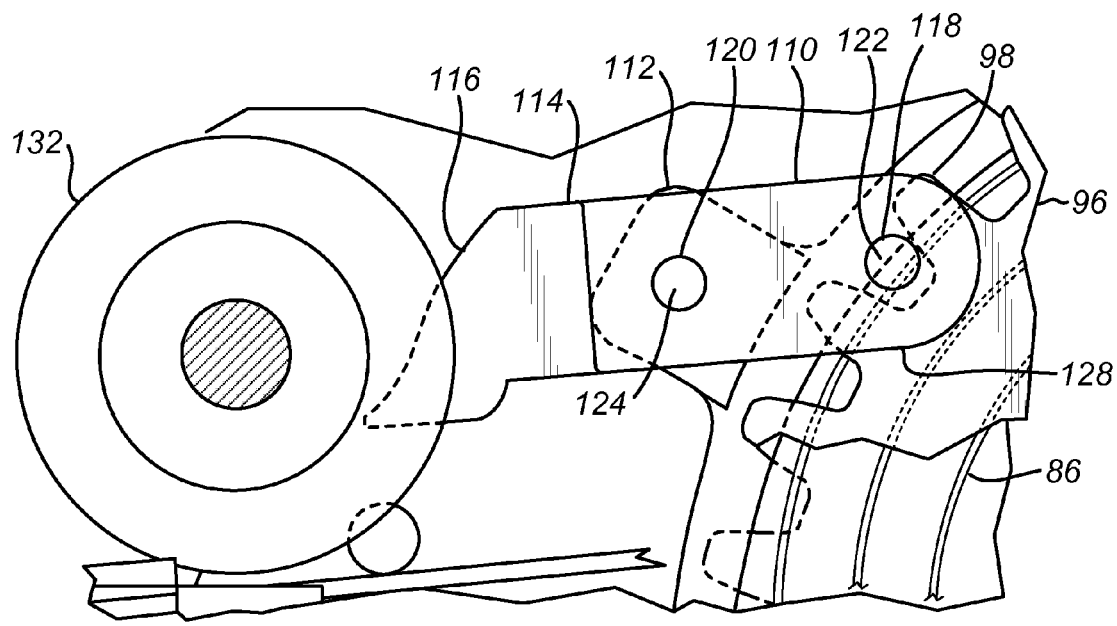
FIGS. 9-14 are detail views of portions of the device of FIG. 4, illustrating interaction of various moving parts.

With reference to FIGS. 3, 5 and 9, a brake 110 is pivotably mounted to a post 112 that extends from the first face 62 of the base 58 at a location distal of, but adjacent to, the ring 82. The brake 110 includes an oblong body 114 having a ramped distal face 116 (FIG. 9). The body 114 includes a first aperture 118 adjacent its proximal end, and a second aperture 120 at or near its center. A first pin 122 extends through the first aperture 118, and a portion of the first pin 122 protrudes from an underside of the body 114 (not visible in the figures). A second pin 124 extends through the second aperture 120 and into an opening 126 (FIG. 3) in the post 112 to pivotably mount the body 114 to the post 112. In alternative embodiments, the pins 122, 124 may be integrally formed with the body 114.

With reference to FIGS. 5 and 9, the body 114 of the brake 110 lies in a plane parallel to that of the gear wheel 96, and a proximal portion 128 of the body 114 overlaps the gear wheel 96. The protruding portion of the first pin 122 extends into the plane of the gear wheel 96 and engages the gear teeth 98 to retain the gear wheel 96 and torsion spring 86 in the wound up condition, as further detailed below.

With reference to FIGS. 3, 5, 8 and 9, the first portion 44 of the housing 42 includes a slot 130 that receives an activation trigger 132. The illustrated slot 130 is L-shaped (FIG. 8), including a transverse leg 134 and a longitudinal leg 136. The trigger 132 is shaped substantially as a mushroom (FIGS. 3 and 5), including an elongate shaft 138 with a bulbous head 140 at a first end. In alternative embodiments, the slot 130 and/or trigger 132 could be any shape.

The shaft 138 extends through the slot 130, with the head 140 lying outside the first portion 44 of the housing 42, as shown in FIG. 4. An underside of the head 140 may abut an outer surface of the first portion 44 of the housing 42, but in alternative embodiments it may be spaced therefrom. With reference to FIG. 3, a ring-shaped collar 142 seats on the shaft 138 inside the housing 42 to prevent withdrawal of the trigger 132 from the slot 130. The collar 142 may bear against an inner surface of the housing 42. The shaft 138 and collar 142 may mate in a friction fit, a threaded engagement, or any other type of engagement.

Figure 8:
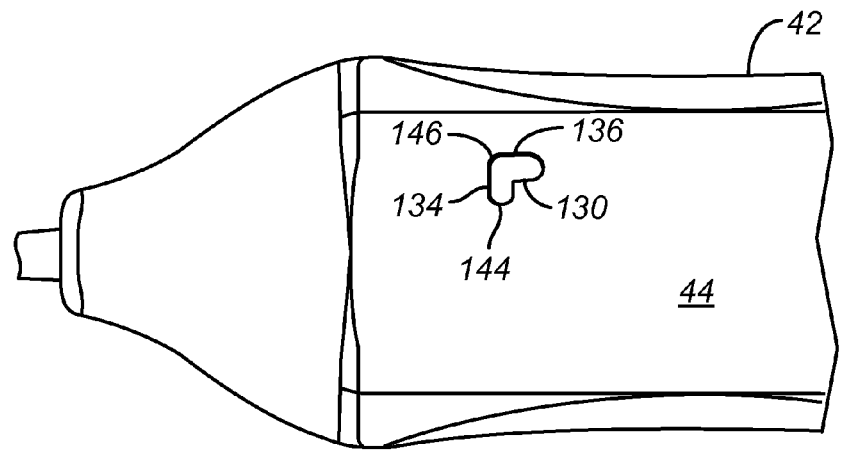
FIG. 8 is a top detail view of a portion of the housing of the device of FIG. 4.

With reference to FIG. 8, in a ready-to-use configuration, the trigger 132 is located at a first end 144 of the transverse leg 134 spaced from a junction 146 of the transverse leg 134 and the longitudinal leg 136 (FIGS. 3, 8 and 9). To activate the device 40, the operator slides the trigger 132 along the transverse leg 134 toward the junction 146 of the transverse leg 134 and the longitudinal leg 136, then proximally along the longitudinal leg 136. Further details about the activated device 40 are described below. Collectively, the trigger 132, the slot 130, and the brake 110 may comprise one embodiment of an activation mechanism. The activation mechanism may, however, include substitute components and/or additional components. For example, in an alternative embodiment the activation mechanism includes the foregoing components plus the torsion spring 96.

Figure 6:
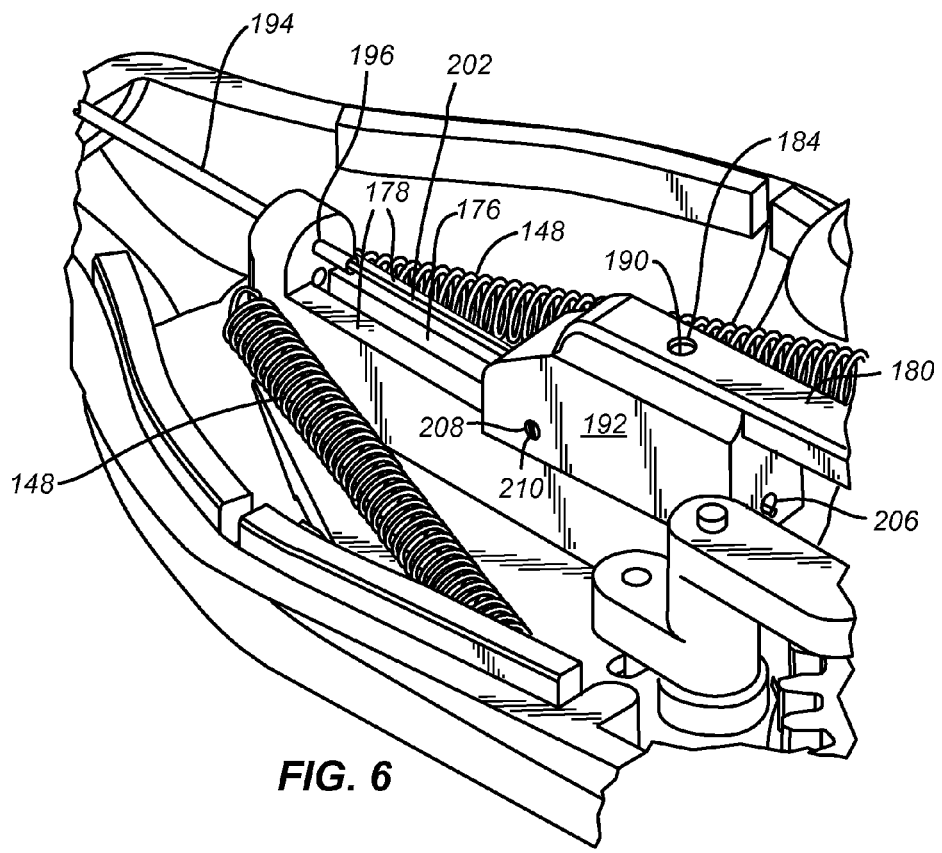
FIG. 6 is a detail view of the portion of FIG. 5 indicated by the area 6-6.

With reference to FIGS. 3, 5 and 6, first and second linear biasing members 148 extend between the base 58 and the housing 42. In the illustrated embodiment, the linear biasing members 148 are coil springs in tension, but could be any other kind of linear biasing members. A distal end of each linear biasing member is secured to a distal end of the base 58, and a proximal end of each linear biasing member is secured to the housing 42 at a location proximal of the distal end of the base 58. The linear biasing members 148 bias the base 58 toward the proximal end of the cavity 50. However, prior to activation, the base 58 is held in position by the ratchet teeth 52 and a pawl 150, as described below.

Figure 7:
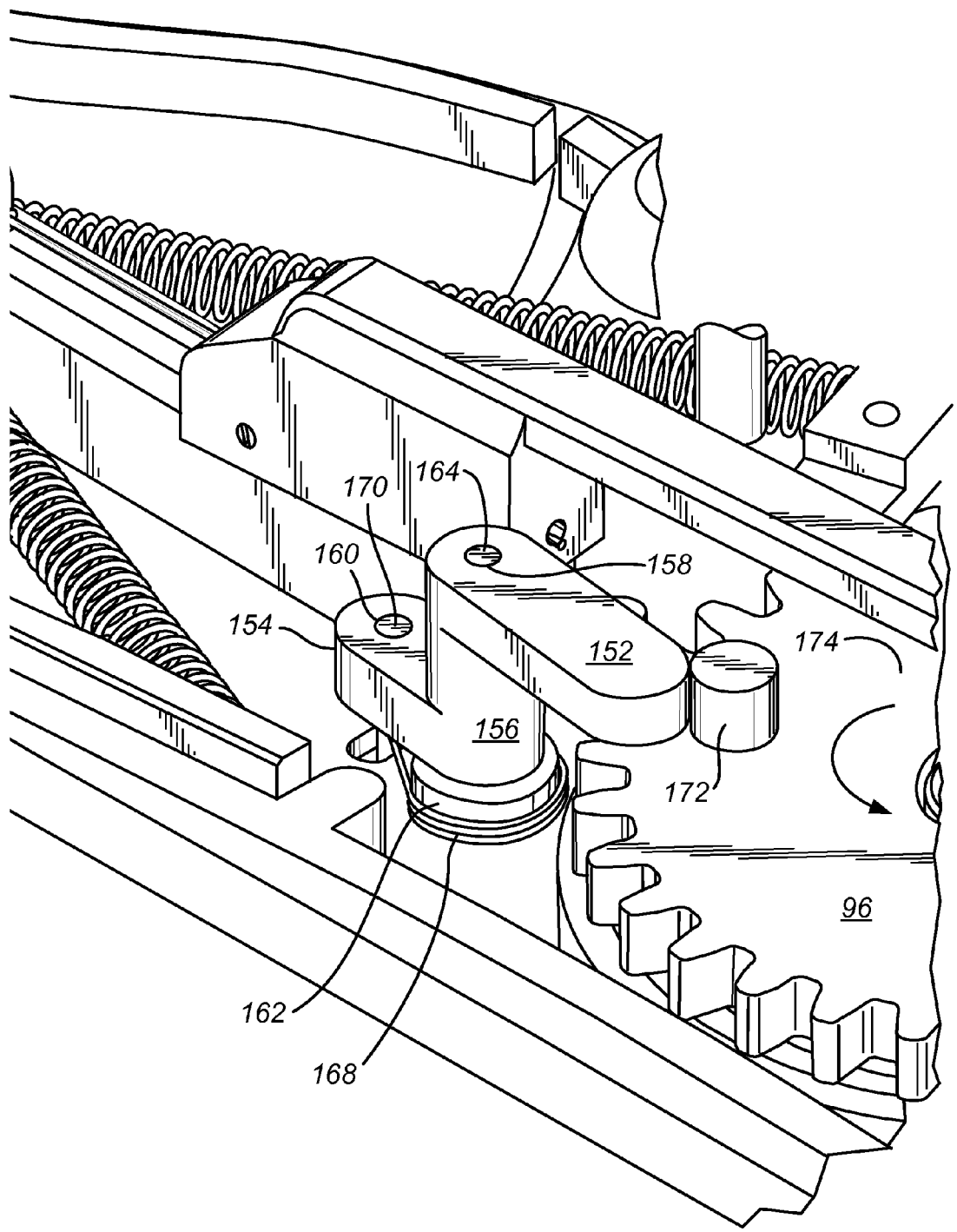
FIG. 7 is a detail view of the portion of FIG. 5 indicated by the area 7-7.

With reference to FIGS. 3, 5 and 7, the pawl 150 comprises first and second planar portions 152, 154 (FIG. 7) spaced from one another, and extending in opposite directions from opposite ends of a column 156 (FIG. 7). A first aperture 158 extends through the column, and a second aperture 160 extends through the second planar portion 154 adjacent a distal end thereof. With reference to FIGS. 3 and 7, the pawl 150 is pivotably mounted on an elevated portion 162 of the first face 62 of the base 58. The elevated portion 162 is located distally of, but adjacent to, the ring 82. A first pin 164 extends through the first aperture 158 and into a recess 166 (FIG. 3) in the elevated portion 162 to effect the pivotable mounting. A biasing member 168 located between the elevated portion 162 and the pawl 150 rotationally biases the pawl 150 counterclockwise. A second pin 170 extends through the second aperture 160 and protrudes from an underside of the second planar portion 60 (not visible in the figures). The second pin 170 engages the ratchet teeth 52, as further described below.

With reference to FIG. 7, the first planar portion 152 of the pawl 150 lies in a plane parallel to that of the gear wheel 96, and a proximal portion of the first planar portion 152 overlaps the gear wheel 96. The gear wheel 96 includes a tab 172 that extends from a face 174 of the gear wheel 96 opposite the torsion spring 86 and adjacent to the gear wheel's periphery. The tab 172 is positioned to contact the first planar portion 152 with each rotation of the gear wheel 96. Upon contact, the pawl 150 pivots clockwise, as shown in FIG. 7, disengaging the second pin 170 from a ratchet tooth 52 with which it is engaged, as further described below.

With reference to FIGS. 2 and 6, the base 58 further comprises a longitudinal track 176, formed by a gap between two parallel walls 178 that extend longitudinally along the base 58 adjacent its distal end. The track 176 guides a distal end of an elongate link rod 180 as it reciprocates, as described in detail below.

With reference to FIGS. 5 and 7, the device 40 further comprises the link rod 180. The link rod 180 includes a proximal end and a distal end, each of which includes an aperture 182, 184. The proximal aperture 182 receives a pin 186 that also extends into an aperture 188 (FIG. 3) in a face of the flywheel 68 adjacent a periphery thereof. The proximal end of the link rod 180 is thus coupled to the flywheel 68 and rotates therewith. With reference to FIG. 6, the distal aperture 184 receives a pin 190 that couples the distal end of the link rod 180 to a block 192. The block 192 abuts the two parallel walls 178, with a protrusion (not shown) extending into the track 176. With reference to FIG. 5, when the flywheel 68 rotates, the distal end of the link rod 180 and the block 192 move in reciprocating motion, due to the proximal end of the link rod 180 being coupled to the flywheel 68 at a location spaced from a center of rotation of the flywheel 68. With reference to FIG. 6, the block 192 thus reciprocates along the walls 178 with the protrusion between the walls 178 guiding the block 192 so that the reciprocating motion follows a defined straight-line path along the track 176. Collectively, the torsion spring 86, the gear wheel 96, the flywheel 68, and the link rod 180 may comprise one embodiment of a reciprocation drive. The reciprocation drive may, however, include substitute components and/or additional components.

With reference to FIGS. 3 and 4, the device 40 further comprises a retractable sheath 194. The retractable sheath 194 is an elongate, flexible, hollow, cylindrical member that extends distally from the housing 42. With reference to FIGS. 5 and 6, a proximal end of the retractable sheath 194 is held in an aperture 196 at a distal end of the base 58. The retractable sheath 194 thus retracts as the base 58 moves proximally within the cavity 50, as described below.

With reference to FIGS. 3, 4 and 4A, the device 40 further comprises a stationary sheath 198. The stationary sheath 198 is an elongate, flexible, hollow, cylindrical member that extends distally from the housing 42. A proximal end of the stationary sheath 198 is held in a nose cone 200 at a distal end of the base 58. In the illustrated embodiment, the nose cone 200 is a flexible conical component secured to the housing 42. The nose cone 200 supports the proximal ends of both the stationary sheath 198 and the retractable sheath 194 to resist buckling and/or kinking. The nose cone 200 may be constructed of rubber, for example, or any other material. In alternative embodiments, the nose cone 200 may be formed integrally with the housing 42, or omitted.

The retractable sheath 194 extends at least partially through a lumen of the stationary sheath 198. The stationary sheath 198 thus provides support for the retractable sheath 194 within. With reference to FIG. 4A, the stationary sheath 198 extends to a point on the retractable sheath 194 near where the distal end of the retractable sheath 194 will be after the device 40 has been activated and the retractable sheath 194 has been retracted, as described further below.

With reference to FIGS. 3, 5 and 6, the device 40 further comprises a reciprocating pushing member 202 extending at least partially through a lumen of the retractable sheath 194. The pushing member 202 includes an elongate shaft 204 (FIG. 3) having a smooth outer surface. With reference to FIG. 6, a proximal end of the pushing member 202 is coupled to the block 192. A longitudinally extending passage 206 in the block 192 receives the pushing member 202. A transversely oriented tapped hole 208 in the block 192 intersects the passage 206. The hole 208 receives a set screw 210, which bears against the pushing member 202 and pins it within the passage 206. Other configurations for coupling the pushing member 202 to the block 192 are within the scope of the present disclosure.

Figure 27:
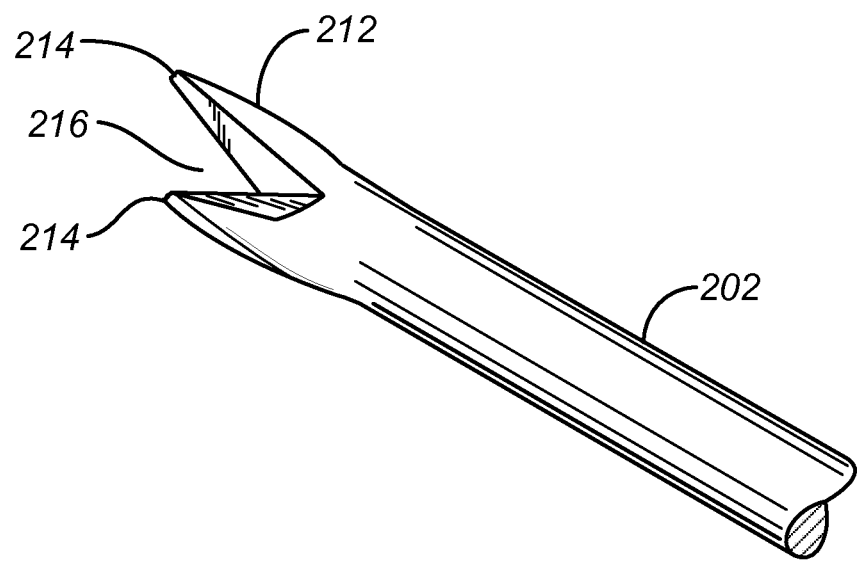
FIG. 27 is a perspective view of a distal end of a pushing member of the devices of FIGS. 3 and 21.
Figure 28:
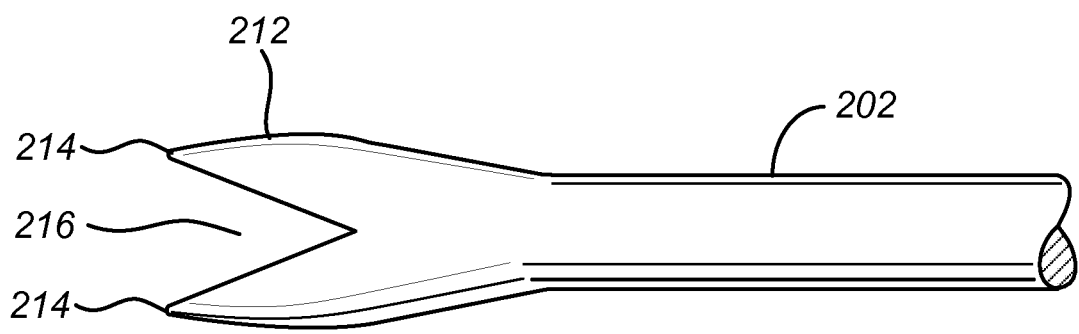
FIG. 28 is a side elevation view of the pushing member of FIG. 27.

Because the pushing member 202 is coupled to the block 192, reciprocating motion of the block 192, described above, induces reciprocating motion of the pushing member 202 within the lumen of the retractable sheath 194. With reference to FIGS. 27 and 28, a distal end of the pushing member 202 includes a fork 212. The fork 212 may be formed integrally with the shaft 138 or may comprise a discrete piece secured to the shaft 138. The illustrated fork 212 includes two diverging tines 214 separated by a V-shaped gap 216. Each tine 214 terminates at a distal end in a fine, but not sharp, point. The fork 212 is configured to incrementally or segmentally push a fibrous implant distally as the pushing member 202 reciprocates within the retractable sheath 194, as described in detail below.

The retractable sheath 194, the stationary sheath 198, and the pushing member 202 are preferably flexible so that they can be guided to a treatment site during a transcervical procedure. These components may comprise, for example, polyether block 192 amide (PEBA, available under the tradename PEBAX®), high-density polyethylene (HDPE), nylon, or other materials. As discussed above, in certain embodiments the forked end 212 of the pushing member 202 may comprise a discrete piece secured to the shaft 138. Where the forked end 212 is a discrete piece, it may for example be formed of stainless steel, or any other material.

Figure 16:
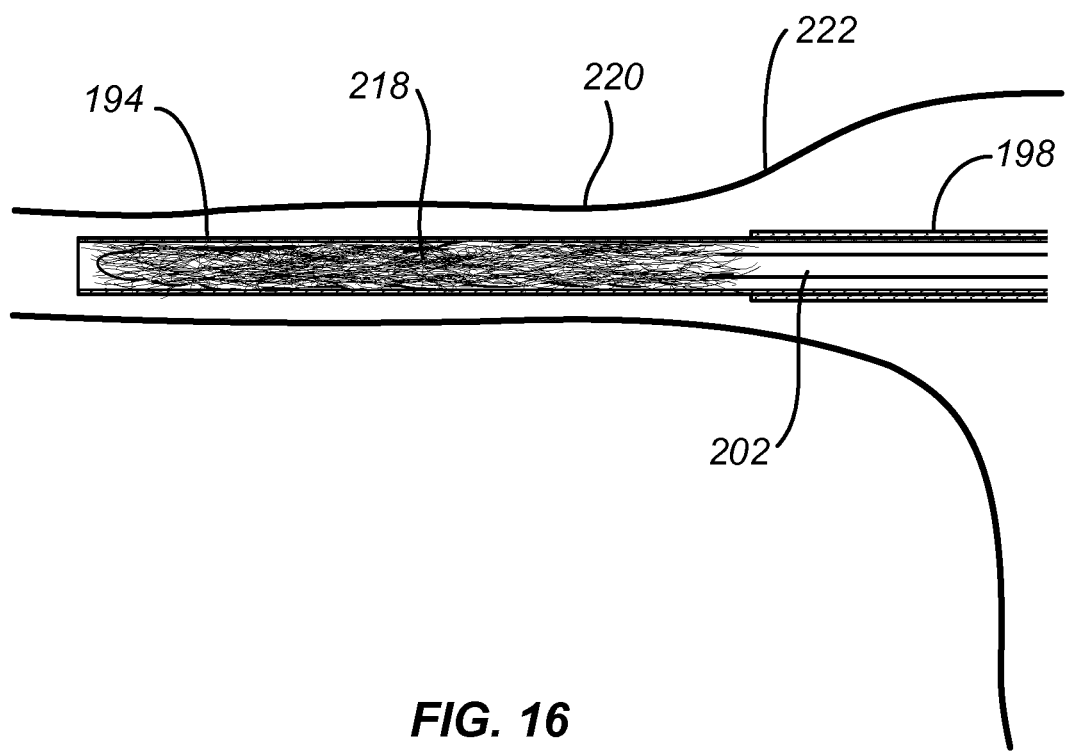

With reference to FIG. 16, the device 40 further comprises an occlusive implant 218 occupying a space around the pushing member 202 and within the retractable sheath 194 lumen. The implant 218 may be a self-expanding fibrous body formed from one or more bioabsorbable materials. The implant 218 may, for example, be similar to or the same as any of the implants described in U.S. Pat. No. 7,815,661. The '661 patent and the present application are commonly owned, and the '661 patent is incorporated herein by reference in its entirety.

In one embodiment, the implant 218 may comprise 240 filaments of 600 denier and 30 cm in length. For example, the implant 218 may comprise 30 filaments of 75 denier with a Z-twist, and 30 filaments of 75 denier with an S-twist. Those filaments combine to make 60 filaments of 150 denier, which is then folded four times to make 240 filaments of 600 denier. The implant 218 may comprise multiple textured and bulked yarns made of biodegradable polymers, such as polylactic acid (PLA), poly-L-lactide (PLLA), or polyglycolic acid (PGA) fibers. The implant 218 may be made from multiple yarns of one biodegradable material type such as PGA, or it can also be a combination of yarns from different materials types, such as PGA and PLLA yarns, mechanically co-mingled to achieve the final implant size and length.

As illustrated in FIG. 16, the occlusive implant 218 occupies the space around the pushing member 202 and within the retractable sheath 194 lumen. As described in further detail below, when the device 40 is activated, the pushing member 202 continuously reciprocates within the retractable sheath 194 lumen as the retractable sheath 194 lumen incrementally retracts proximally. With each distal stroke of the pushing member 202, the tines 214 of the fork 212 urge the fibrous implant 218 material into the V-shaped gap 216 between the tines 214 and push the implant 218 distally with respect to the retractable sheath 194. However, the smooth taper of the outer surfaces of the fork 212 enable the fork 212 to slide proximally through the implant 218 on the return stroke without snagging the implant 218.

The reciprocating motion of the pushing member 202 coupled with the retraction of the retractable sheath 194 incrementally or segmentally expels the implant 218 from the retractable sheath 194. A lubricious coating may be applied to the inner surface of the retractable sheath 194 and/or the outer surface of the pushing member 202 to reduce the friction experienced by the implant 218 as it is expelled from the retractable sheath 194. Preferably, a portion of the implant 218 extends distally past the fork 212 in the ready to use configuration. Thus, the implant 218 immediately begins the incremental expulsion as soon as the device 40 is activated. Since the implant 218 is self-expanding, as it is expelled it expands to fill the space of the fallopian tube and thereby occlude the tube.

Operation

FIGS. 15-19 illustrate operation of any of the device 40 or the device 240 (or the device 30 or the device 37, where corresponding components of the device 30/37 are substituted for the illustrated and described ones of the device 40/240) in a method of delivering the implant 218 to a fallopian tube 220, e.g. to occlude the fallopian tube.

Figure 15:
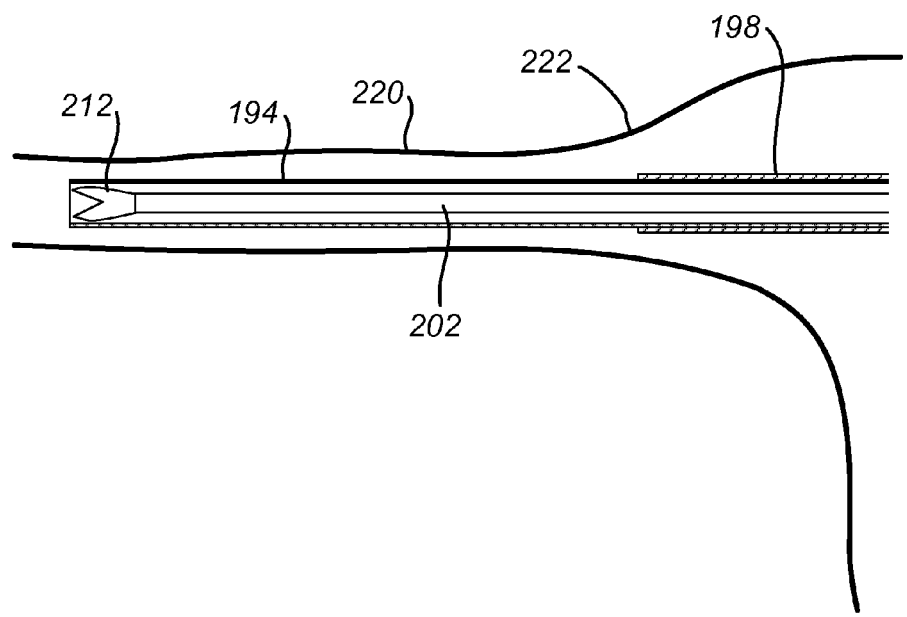
FIGS. 15-19 are side elevation views of a distal portion of the device of FIG. 4 at successive stages of a procedure for delivering an implant.
Figure 17:
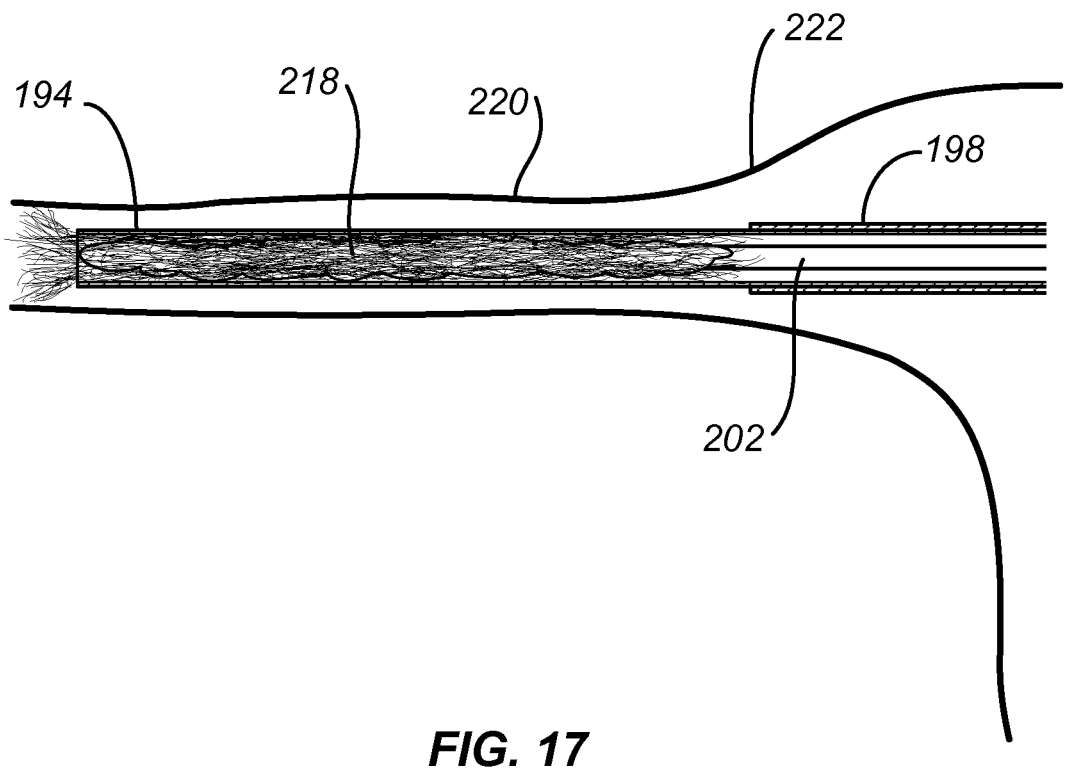

The fallopian tube 220 may be accessed transcervically to position the distal end of the stationary sheath 198 at or near the ostium 222, or other desired location in the fallopian tube 220. A hysteroscope (not shown) may be used to access the uterus and/or the ostium 222, and the sheaths 194, 198 may be advanced through a lumen of the hysteroscope until the distal ends of the sheaths 194, 198 are positioned at or near the ostium 222, e.g. as shown in FIGS. 15-17. Instead of or in addition to hysteroscopic access, external visualization, such as ultrasound or fluoroscopy, may be used to aid in guiding the sheaths. The distal end of the stationary sheath 198 may include a marker band (not shown) to aid in external visualization. The marker band may be, for example, radiopaque, or any other kind of marker band.

The stationary sheath 198 is preferably left or held stationary (or substantially stationary) relative to the fallopian tube 220 while the implant 218 is expelled from the retractable sheath 194. Thus, the operator can simply hold the housing 42 stationary during implant expulsion, or leave it fixed to a stationary location such as an operating chair or table during implant expulsion. The device 40 therefore does not burden the operator with manually retracting the device 40 during implant expulsion; instead, the operator holds or fixes a portion of the device 40 stationary during implant expulsion while activating another portion of the device (e.g., the retractable sheath 194 and the pushing member 220) to retract relative to the held/fixed portion as the implant is expelled into the HAS.

When proper positioning of the sheaths 194, 198 has been verified, the operator activates the device 40. The reciprocation drive reciprocates the pushing member 202 within the retractable sheath 194, and the pushing member 202 incrementally expels the implant 218 from the end of the sheath 194.

The retractable sheath 194 and the pushing member 202 retract proximally toward and into the stationary sheath 198 as the pushing member 202 reciprocates and expels the implant 218. Where the device employs an active retraction drive (e.g., in the case of the device 30 or the device 40), the initiation and rate of retraction are substantially predetermined by the mechanical characteristics of the retraction drive. Where the device employs a passive retraction drive (e.g., in the case of the device 37 or the device 240), the retractable sheath 194 and pushing member 202 retract when the implant 218 has been packed in the fallopian tube 220 to a sufficient density to develop sufficient back pressure acting on the retractable sheath 194 and/or pushing member 202 to overcome the distally-directed force exerted by the retraction drive (e.g., by the biasing members 148). The retractable sheath 194 and the pushing member 202 will continue retracting so long as this condition prevails.

Figure 18:
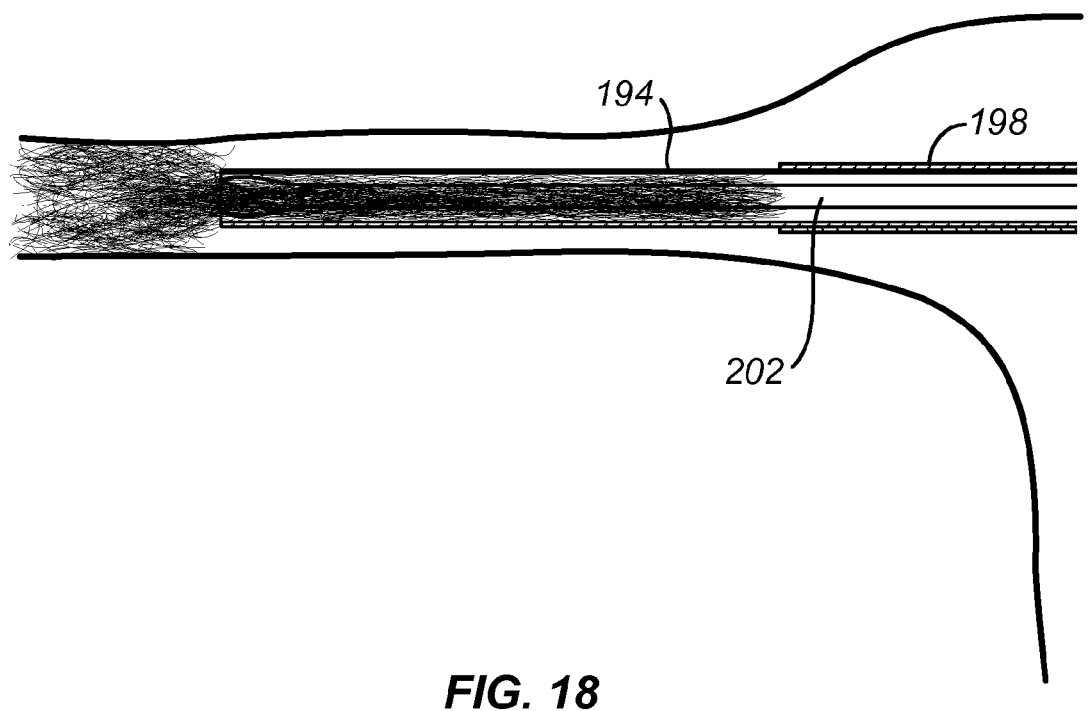
Figure 19:
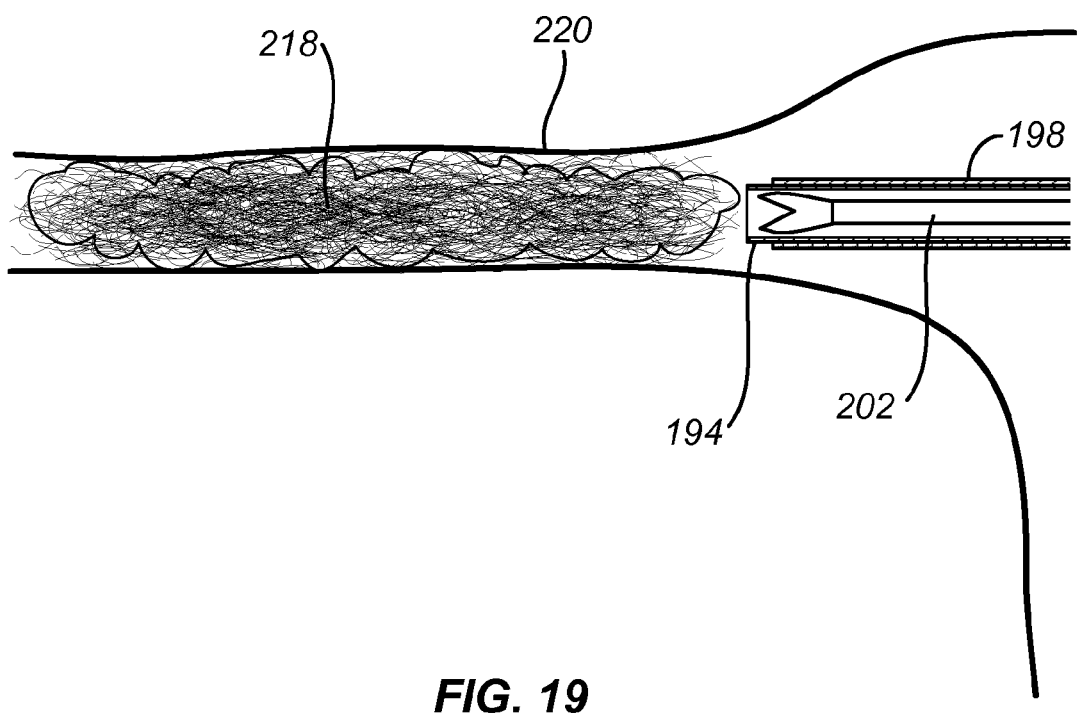

As seen in FIGS. 17-19, expulsion of the implant 218 and retraction of the sheath 194 continue until the entire implant 218 has been expelled into the fallopian tube 220 and the sheath 194 has retracted partially or completely into the stationary sheath 198. The expelled portion of the implant 218 can self-expand to span the width of the HAS, as seen in FIG. 19.

The device 40 and any hysteroscope can then be withdrawn from the uterus and the implant 218 left in place to occlude the fallopian tube 220. The delivered implant 218 is preferably sufficiently dense to prevent ova or sperm from traveling therethrough, while allowing tissue ingrowth through the implant 218 to create an occlusion with ingrown scar tissue. Where the implant 218 is bioabsorbable, it is absorbed into the scar tissue to generate and leave an occlusion of the fallopian tube 220 comprising scar tissue with substantially no implant material therein.

If desired, the operator may perform an occlusion of a second fallopian tube of a patient in the manner described herein (e.g., using a second device 30/37/40/240), after performing a occlusion of the first fallopian tube in the manner described herein. Thus the patient may be sterilized.

Preferably, the device 40/240 is configured so that the pushing member 202 (including the distal tip thereof) remains within the lumen of the retractable sheath 194 throughout (a) the range of reciprocation of the pushing member 202, (b) the expulsion of the implant 218, (c) the retraction of the retractable sheath 194, and/or (d) the entire procedure of implanting the implant 218 into the fallopian tube 220. (The pushing member 202 retracts as it reciprocates, but the retractable sheath 194 retracts along with it.) As a result, the risk of striking and injuring the fallopian tube and/or other structures with the reciprocating pushing member 202 is minimized or eliminated.

The methods of using the device 30/37/40/240 described herein usually involve the delivery of the implant 39/240 into a fallopian tube. However, it should be understood that the same methods may be employed to deliver the implant to other types of HAS, such as a blood vessel. The blood vessel may be a vein or an artery. The vein may be a vein in a leg of a patient. The leg may have one or more varicose veins.

Figure 10:
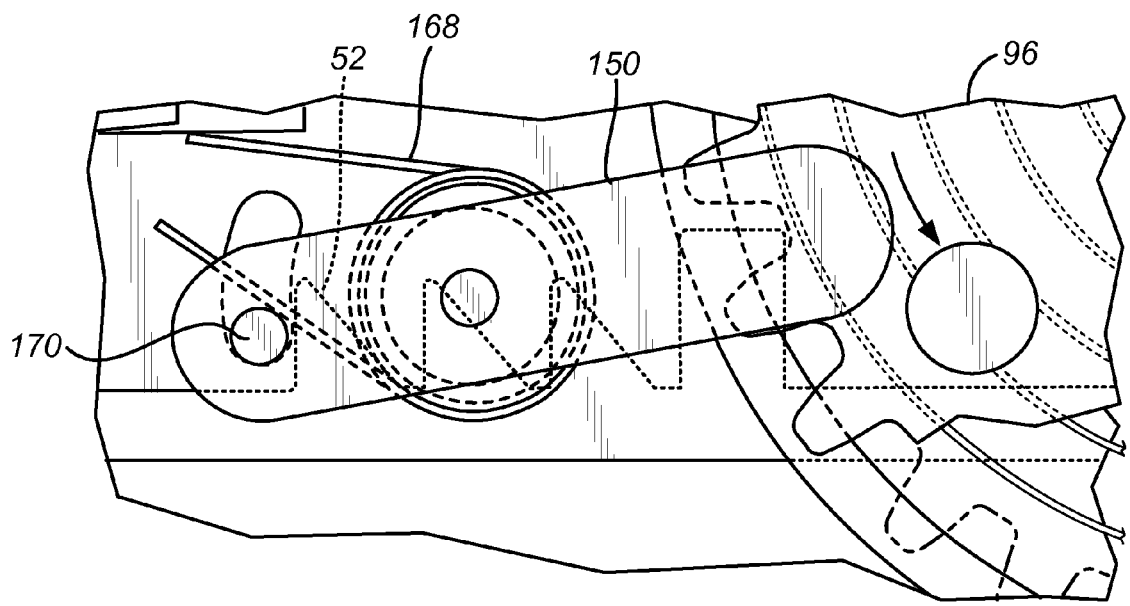

A discussion of methods of operating the device 40 will now be provided, with additional detail relating to the specific mechanisms disclosed. FIGS. 5 and 9-19 illustrate operation of the device 40 described above. FIGS. 5, 9, 10, 15 and 16 show the device 40 in the ready to use configuration. With reference to FIG. 9, the first pin 122 of the brake 110 resides in a space between adjacent gear teeth 98, resisting rotation of the gear wheel 96 against the biasing force of the torsion spring 86. With reference to FIG. 10, the second pin 170 of the pawl 150 resides in a space distal of the distal-most ratchet tooth 52, bearing against the ratchet tooth 52 and resisting translation of the base 58 against the biasing force of the linear biasing members 148 (FIG. 5). The rotational biasing member bearing 168 on the pawl 150 retains the second pin 170 of the pawl 150 in this position. The arrow in FIG. 10 illustrates the direction of rotation for the gear wheel 96 upon device 40 activation. With reference to FIGS. 15 and 16, a distal portion of the retractable sheath 194 extends from a distal end of the stationary sheath 198. The distal portion of the retractable sheath 194 is disposed within the fallopian tube 220 with the distal end of the stationary sheath 198 positioned at or near the ostium 222. The fork 212 is positioned just inside a distal end of the retractable sheath 194, with the occlusive implant 218 occupying the space around the pushing member 202 and within the retractable sheath lumen.

The fallopian tube 220 may be accessed transcervically to position the distal end of the stationary sheath 198 at or near the ostium 222, or other desired location in the fallopian tube 220. A hysteroscope (not shown) may be used to access the uterus and/or the ostium 222, and the sheaths 194, 198 may be advanced through a lumen of the hysteroscope until the distal ends of the sheaths 194, 198 are positioned at or near the ostium 222, e.g. as shown in FIGS. 15-17. Instead of or in addition to hysteroscopic access, external visualization, such as ultrasound or fluoroscopy, may be used to aid in guiding the sheaths. The distal end of the stationary sheath 198 may include a marker band (not shown) to aid in external visualization. The marker band may be, for example, radiopaque, or any other kind of marker band. Advantageously, the housing 42 is compact enough to be held with one hand. The operator's other hand can thus be used to control an external visualization device, so that the implantation procedure can be performed by a single operator.

Figure 11:
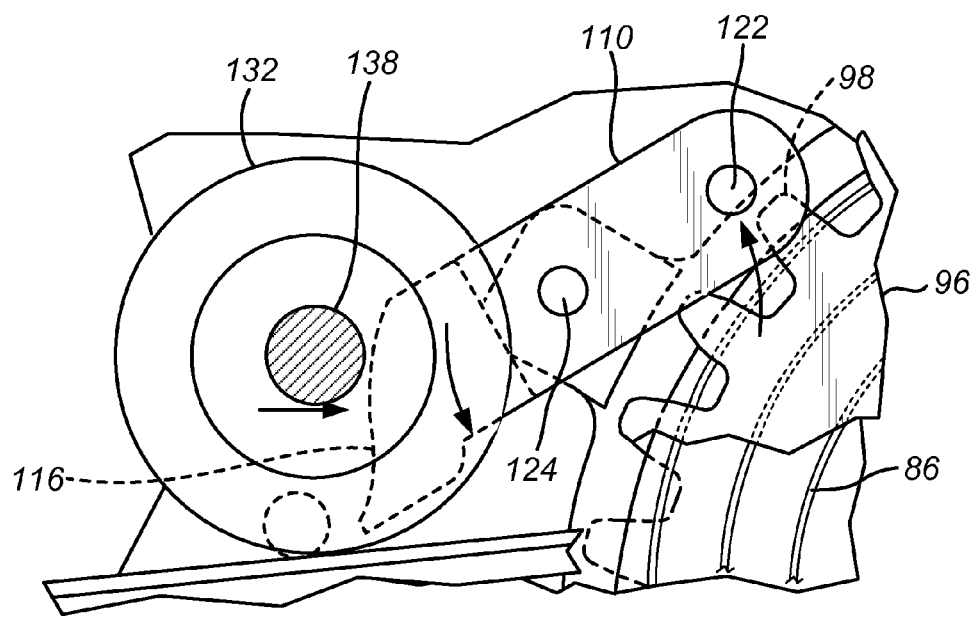

When proper positioning of the sheaths 194, 198 has been verified, the operator activates the device 40. To activate the occlusive implant delivery device 40, the operator slides the trigger 132 (FIG. 4) along the transverse leg 134 toward the junction of the transverse leg 134 and the longitudinal leg 136, then proximally along the longitudinal leg 136 (FIG. 8). For example, the operator may manipulate the trigger 132 with his or her thumb on the same hand that is holding the housing 42. With reference to FIG. 11, movement of the trigger 132 proximally along the longitudinal leg 136 brings the shaft 138 into contact with the ramped distal face 116 of the brake 110, causing the brake 110 to rotate counterclockwise about the second pin 124. The rotation disengages the first pin 122 from the gear teeth 98. Once disengaged from the brake 110, the gear wheel 96 rotates counterclockwise as the stored energy in the torsion spring 86 is released.

With reference to FIG. 5, counterclockwise rotation of the gear wheel 96 induces clockwise rotation of the flywheel 68, due to the engagement of the gear teeth 98 with the flywheel teeth 70. Rotation of the flywheel 68 induces reciprocal longitudinal motion of the link rod 180, which in turn induces reciprocal motion of the pushing member 202. The protrusion on the underside of the block 192 rides back and forth along a reciprocation axis that extends along the track 176 (FIG. 6). The block 192 rotates back and forth over a small angle due to the circular motion of the proximal end of the link rod 180. The pushing member 202 preferably has sufficient flexibility to accommodate this rotational motion.

Figure 12:
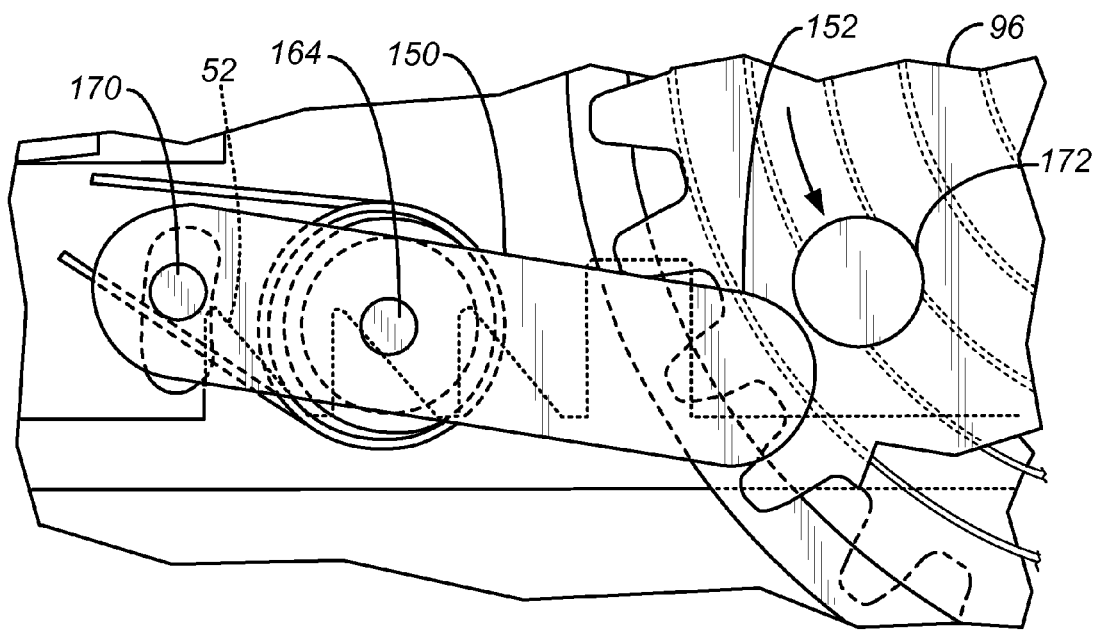
Figure 13:
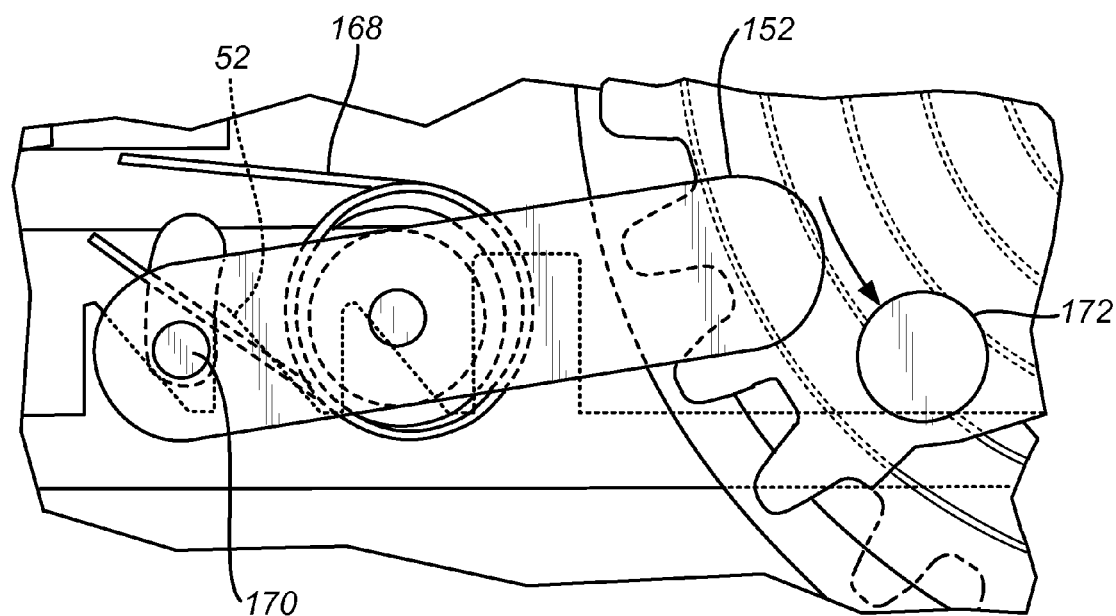

With reference to FIG. 17, reciprocal longitudinal motion of the pushing member 202 incrementally or segmentally expels the fibrous implant 218 from the retractable sheath 194. Once expelled, the implant 218 self-expands to fill and occlude the fallopian tube 220. With reference to FIGS. 7 and 12, continued counterclockwise rotation of the gear wheel 96 brings the tab 172 into contact with the first planar portion 152 of the pawl 150, rotating the pawl 150 clockwise about the first pin 164. Clockwise rotation of the pawl 150 moves the second pin 170 out of engagement with the distal-most ratchet tooth 52 (FIG. 12). Once the second pin 170 disengages the distal-most ratchet tooth 52, tension in the linear biasing members 148 (FIG. 5) moves the base 58 proximally within the cavity 50. Engagement of the base rails 56 with the housing rails 64 guides the longitudinal movement of the base 58 with respect to the housing 42. Collectively, the torsion spring 86, the gear wheel 96 with the tab 172, the pawl 150, the ratchet teeth 52, and the linear biasing members 148 may comprise one embodiment of a retraction drive. The retraction drive may, however, include substitute components and/or additional components.

As the base 58 retracts within the housing 42, it pulls the retractable sheath 194 and the pushing member 202 with it, since both are coupled to the base 58. However, with reference to FIG. 13, when the tab 172 has passed the first planar portion 152, the second pin 170 of the pawl 150 snaps into the next proximal ratchet tooth 52 under the influence of the rotational biasing member 168. Engagement of the second pin 170 and the next proximal ratchet tooth 52 arrests further movement of the base 58 and the retractable sheath 194. Thus, as shown in FIG. 18, the retractable sheath 194 and the pushing member 202 withdraw proximally by the distance between adjacent ratchet teeth 52. In one embodiment, adjacent ratchet teeth 52 are separated by approximately 0.150", for a total length of approximately 0.450" (4×0.150") from the distal-most ratchet tooth 52 to the proximal-most ratchet tooth 52.

Figure 14:
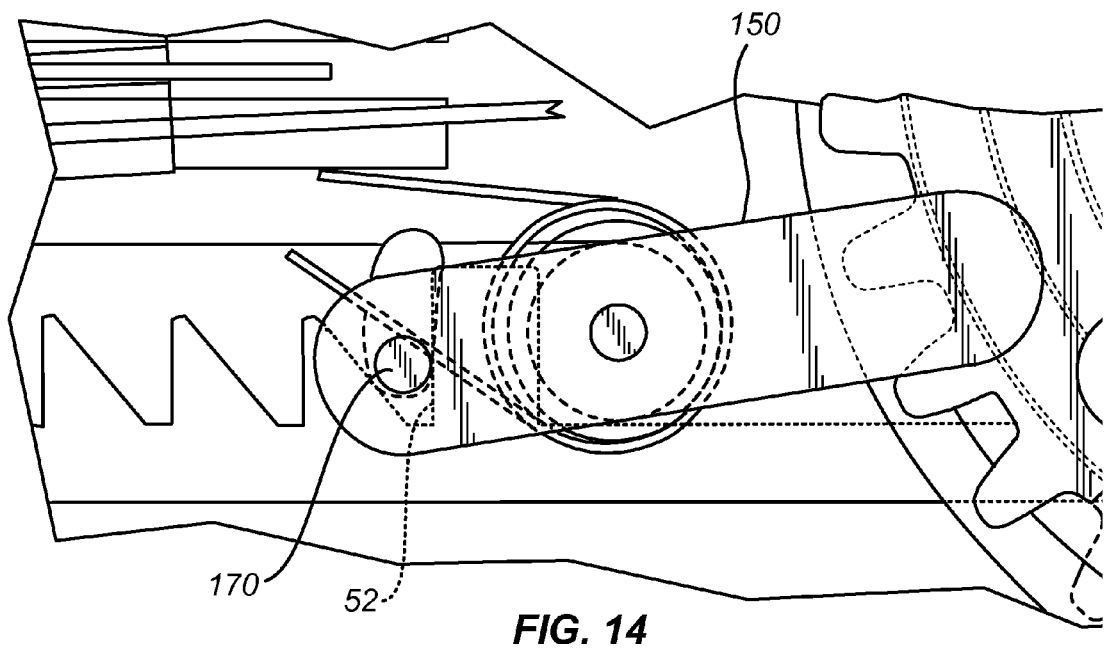

The reciprocal motion of the pushing member 202 and the incremental withdrawal of the retractable sheath 194 and the pushing member 202 continue until the second pin 170 of the pawl 150 reaches the proximal-most ratchet tooth 52, as shown in FIG. 14. At this point, the implant 218 has been completely expelled from the retractable sheath 194, as shown in FIG. 19. The implant 218 completely occludes the fallopian tube 220 over a predetermined distance so that ova cannot pass in a downstream direction, and sperm cannot pass in an upstream direction. While FIG. 19 illustrates the retractable sheath 194 protruding from the stationary sheath 198, in an alternative embodiment when the implant 218 has been completely expelled, the retractable sheath 194 may not extend beyond the stationary sheath 198.

With reference to FIG. 5, a gear ratio of the gear wheel 96 to the flywheel 68 is greater than 1:1. Thus, for each rotation of the gear wheel 96 the flywheel 68 completes more than one rotation, meaning that the pushing member 202 cycles more than one time for each rotation of the gear wheel 96. In one embodiment, the gear ratio is 1:2.3. When combined with the above embodiment in which adjacent ratchet teeth 52 are separated by approximately 0.113", this gear ratio causes the delivery of 2.3 stroke lengths or portions of the implant 218 material per 0.113" of fallopian tube 220, because each rotation of the gear wheel 96 withdraws the retractable sheath 194 by 0.113" while the pushing member 202 cycles 2.3 times. And, four rotations of the gear wheel 96 across the four ratchet teeth 52 induces approximately nine rotations of the flywheel 68 (4×2.3=9.2). Multiple cycles of the pushing member 202 per rotation of the gear wheel 96 tightly packs the implant 218 into the fallopian tube 220, increasing its density and/or radial bulk, and urging it to expand to better occlude the fallopian tube 220.

FIGS. 15-28 illustrate another embodiment of the present occlusive implant delivery devices and associated methods. This embodiment combines reciprocal motion with passive retraction in response to back pressure, and may be used to perform methods of delivering an implant to an HAS such as a fallopian tube, including but not limited to the methods of FIGS. 16-19 and 25-26, as described below. The embodiment of FIGS. 15-28 can be generally similar in structure and function to the embodiment of FIGS. 2A and 2B or to the embodiment of FIGS. 3-19, except as further described herein. For example, the stationary sheath 198, retractable sheath 194, pushing member 202, occlusive implant 218 and housing 242 of the delivery device 240 of FIGS. 15-28 can be similar in structure and function to the first sheath 31, second sheath 32, pushing member 33, occlusive implant 39 and housing 41, respectively, of the delivery device 30 of FIGS. 2A and 2B; and vice versa. In the device 240 of FIGS. 15-28, the powered drive member 280 and the components forming a drivetrain from the powered drive member 280 to the pushing member 202 collectively form a reciprocation drive which can be employed as the reciprocation drive 34 in the device 30 of FIGS. 2A-2B (or in the device 30 of FIGS. 1A-1B, or in the device 40 of FIGS. 3-19, 27 and 28). In the device 240 of FIGS. 15-28, the linear biasing member 148 and the components (rails 260, rails 268, etc.) that direct the retraction of the retractable sheath 194, pushing member 202, etc., collectively form a retraction drive which can be employed as the retraction drive 43 in the device 30 of FIGS. 2A-2B.

Figure 20:
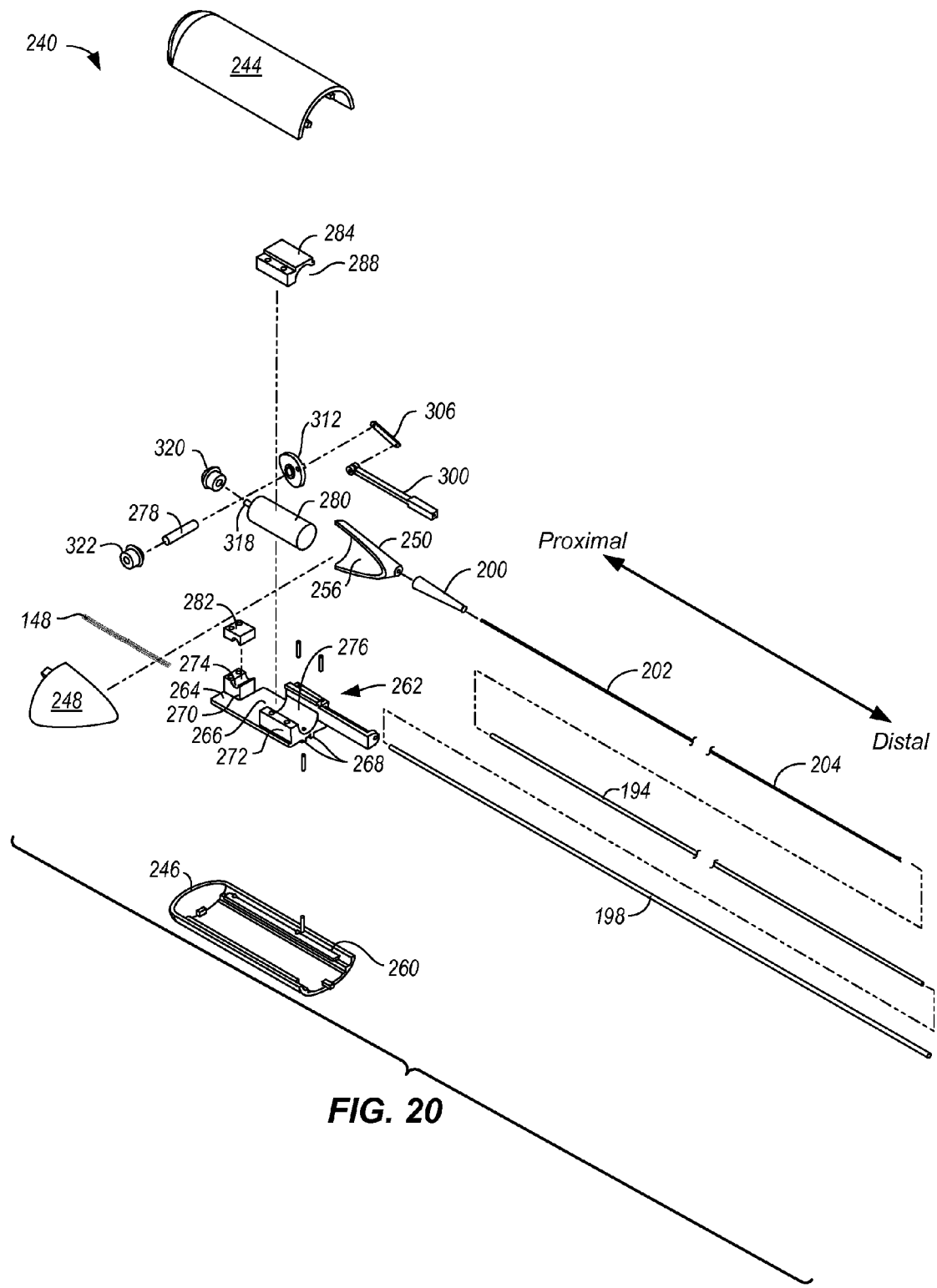
FIG. 20 is an exploded perspective view of another embodiment of the present occlusive implant delivery devices.
Figure 21:
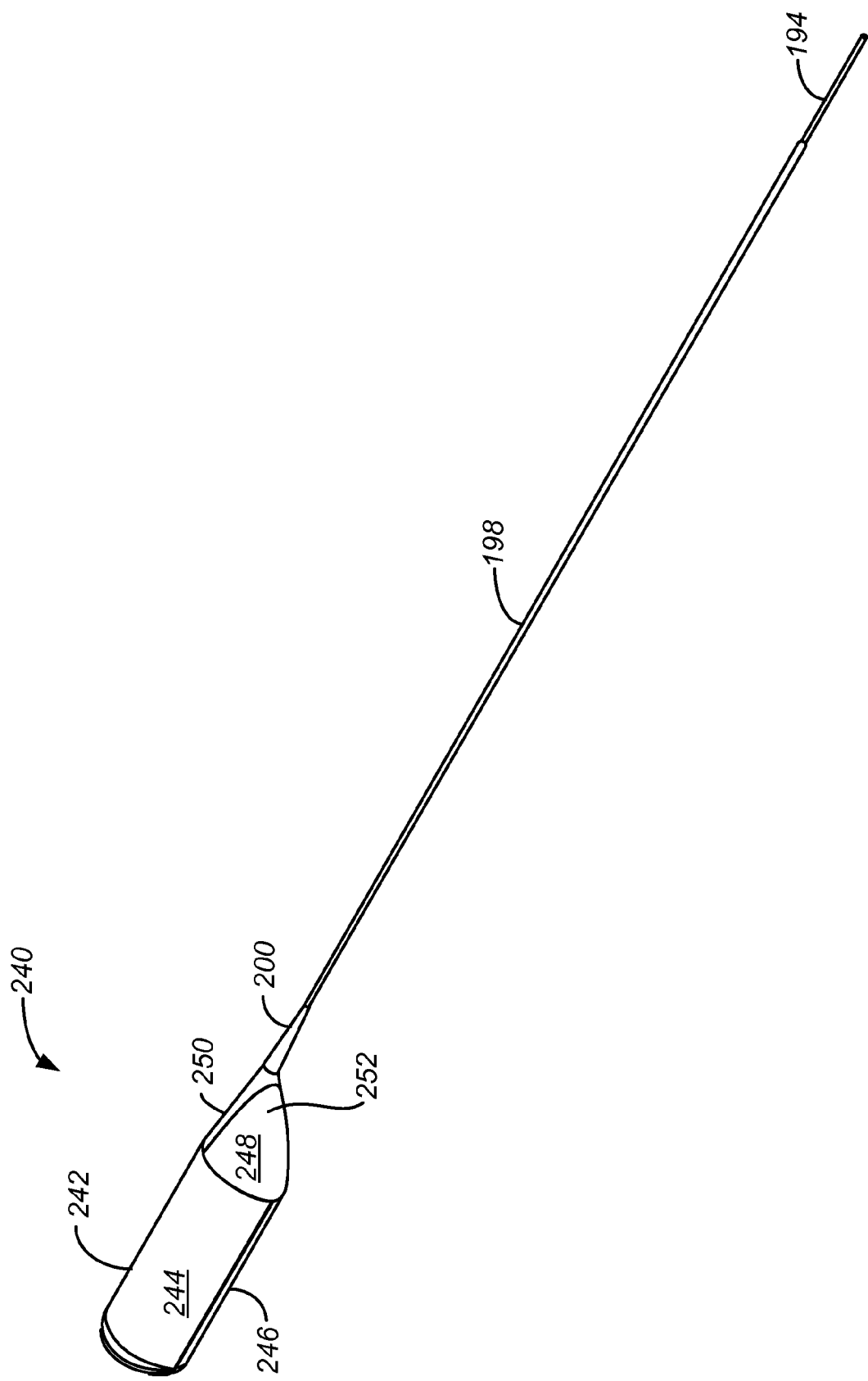
FIG. 21 is an assembled perspective view of the device of FIG. 20.
Figure 22:
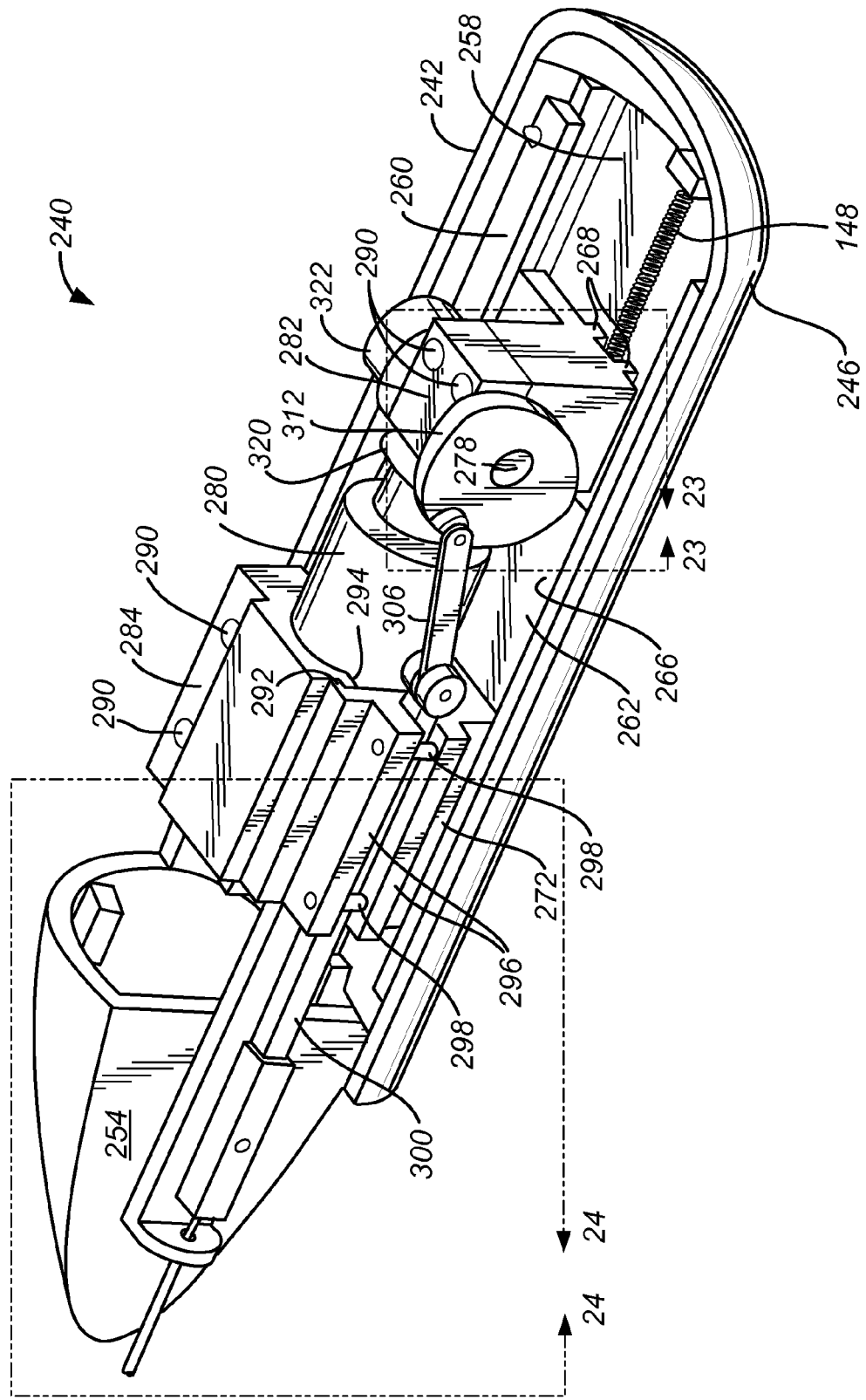
FIG. 22 is a perspective view of the device of FIG. 21 with portions of the housing removed.

With reference to FIGS. 20-22, the illustrated delivery device 240 includes a housing 242 defining a body of the apparatus. As shown in FIG. 20, the housing 242 includes first, second, third and fourth portions 244, 246, 248, 250 that may be secured to one another in any suitable fashion, such as a snap fit, adhesive, welding, etc. The housing 242 may be of a suitable size and shape to be comfortably held by an operator with one hand. In the illustrated embodiment, the first portion 244 is shaped substantially as a half-cylinder, the second portion 246 is shaped substantially as a rectangular plate with rounded corners at a proximal end, the third portion 248 has a convex outer surface 252, a flat outer surface 254 (FIG. 22), and a triangular profile, and the fourth portion 250 also has a triangular profile and contains a recess 256 (FIG. 20). However, the housing 242 can have any shape. The housing 242 may be constructed of any suitable material, such as an injection molded plastic.

With reference to FIG. 22, the housing 242 includes an interior cavity 258 that receives and retains a plurality of components that are described in further detail below. The second portion 246 further includes a pair of spaced side rails 260 that extend longitudinally along opposing sidewalls 296. The functionality of the rails 260 is described below.

With reference to FIGS. 20 and 22, the cavity receives a base 262, which is configured to move within the cavity along a longitudinal axis of the device 240. With reference to FIG. 20, the base 262 includes a planar portion 264 and a plurality of structures that protrude from a first face 266 thereof. A second face, opposite the first face 266, includes a pair of closely spaced rails 268 that extend longitudinally. The functionality of the rails 268 is described below.

With reference to FIG. 20, a proximal support 270 and a distal support 272 extend from the first face 266 of the base 262. Each support 270, 272 is shaped substantially as a rectangular block with an upward-facing semi-cylindrical cutout 274, 276. With reference to FIGS. 20 and 22, the cutout 274 of the proximal support 270 receives a cylindrical axle 278, and the cutout 276 of the distal support 272 receives a powered drive member 280. In one embodiment the powered drive member 280 is an electric motor, which may be a DC motor. Proximal and distal clamp members 282, 284 overlie the axle 278 and powered drive member 280, respectively. Each clamp member 282, 284 is shaped substantially as a rectangular block with a downward-facing semi-cylindrical cutout 286, 288. Together, each support 270, 272 and its corresponding clamp member 282, 284 form a cylindrical space that receives the axle 278 and the powered drive member 280. With reference to FIG. 22, fastening members 290 secure each clamp member 282, 284 to its corresponding support 270, 272. The fastening members may be screws, bolts, pins, or any other type of fastening member. In addition, the distal support 272 includes a longitudinally extending inner lip 292 that overlaps a longitudinally extending inner lip 294 on the distal clamp member 284 to secure the two components 272, 284 to one another.

With continuing reference to FIG. 22, a side of the distal support 272 includes first and second spaced parallel walls 296 that extend longitudinally. A pair of spaced posts 298 extends between the walls 296. A space between the walls 296 receives a piston 300. The piston 300 is shaped substantially as an elongate bar with a rectangular cross-section, but could have any cross-sectional shape. With reference to FIG. 22, a proximal end of the piston 300 includes spaced furcations 302. Each furcation 302 is shaped as a circular disk and includes a central aperture 304. A space between the furcations 302 receives a distal end of a link rod 306. The link rod 306 is a flat bar with an aperture 308 at each end. A fastening member 310, such as a pin, passes through the apertures 304 in the furcations 302 and the distal aperture 308 in the link rod 306, thereby pivotably joining the link rod 306 to the piston 300.

Figure 23:
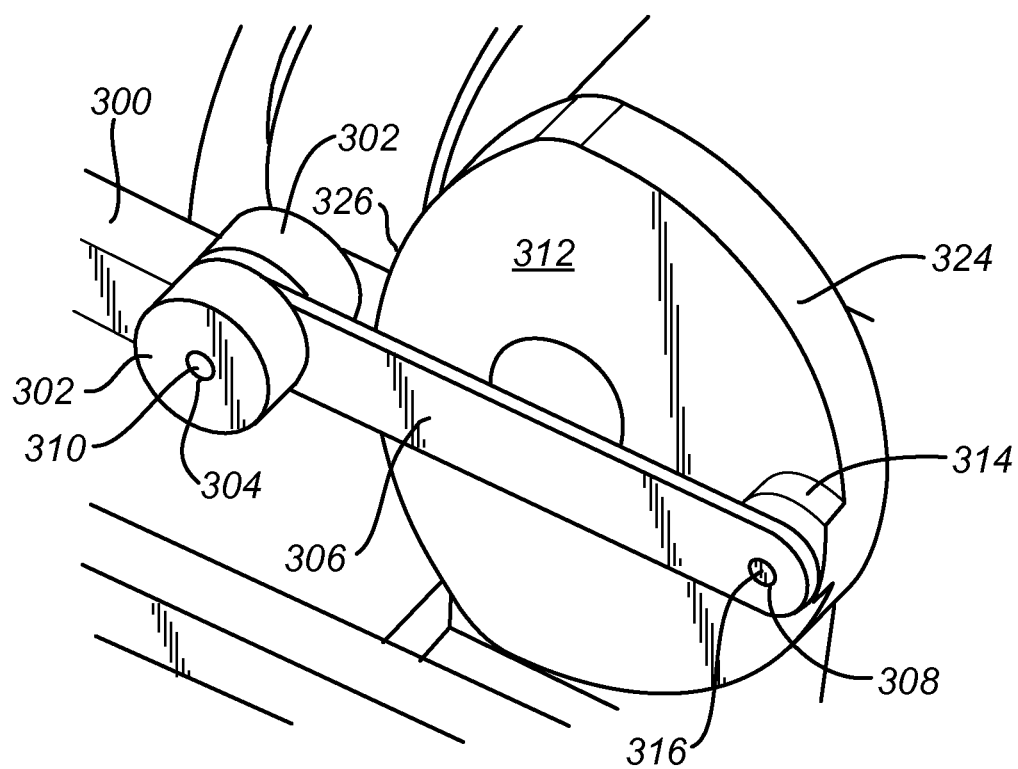
FIG. 23 is a detail view of the portion of FIG. 22 indicated by the area 23-23.

With reference to FIGS. 22 and 23, a first end of the axle 278 receives a flywheel 312. With reference to FIG. 22, the flywheel 312 includes a raised portion 314 in its outward face, near an edge thereof. The raised portion 314 includes an opening (not visible in the figures). The proximal end of the link rod 306 abuts the raised portion 314, with the proximal aperture 308 overlying the opening in the raised portion 314. A fastening member 316, such as a pin, passes through the aperture 308 in the link rod 306 and into the opening in the flywheel 312, thereby pivotably joining the link rod 306 to the flywheel 312.

With reference to FIGS. 20 and 22, an output shaft 318 of the powered drive member 280 receives a first bevel gear 320. A second end of the axle 278, opposite the flywheel 312, receives a second bevel gear 322. The bevel gears 320, 322 mate, such that rotation of the output shaft 318 induces rotation of the axle 278 and the flywheel 312. Rotation of the flywheel 312 induces reciprocal longitudinal motion, through the link rod 306, of the piston 300 in the space between the walls 296 of the distal support 272. This reciprocal longitudinal motion is transmitted to a pushing member 202, as described below.

With reference to FIG. 22, the flywheel 312 includes an eccentric periphery comprising a first semi-circular edge 324 with a first radius, and a second semi-circular edge 326 with a second radius. The raised portion 314 is located at or near the center of the first edge 324. The first radius is smaller than the second radius. Thus, when the flywheel 312 rotates, at the instant that the raised portion 314 is in its most proximal position there is a gap between the piston 300 and the flywheel 312. The eccentric periphery thus prevents interference between the piston 300 and the flywheel 312.

With reference to FIGS. 20 and 22, a linear biasing member 148 extends between the base 262 and a proximal end of the second portion 246 of the housing 242. As shown in FIG. 22, the linear biasing member 148 extends longitudinally between the rails 268 on the second surface of the base 262. While not visible in the figures, a distal end of the linear biasing member 148 connects to the base 262 and a proximal end of the linear biasing member 148 connects to the second portion 246 of the housing 242. In the illustrated embodiment, the linear biasing member 148 is a coil spring, but could be any other type of linear biasing member 148. The linear biasing member 148 is either at equilibrium, or under a small amount of compression. The linear biasing member 148 thus biases the base 262 in the distal direction with respect to the housing 242.

With reference to FIGS. 20 and 21, the occlusive implant delivery device 240 further comprises a retractable sheath 194, a stationary sheath 198, a nose cone 200, and a pushing member 202. These components are substantially identical to their counterparts discussed above with respect to FIGS. 3-19. They will thus not be further described here, except to describe their relationships to other components.

Figure 24:
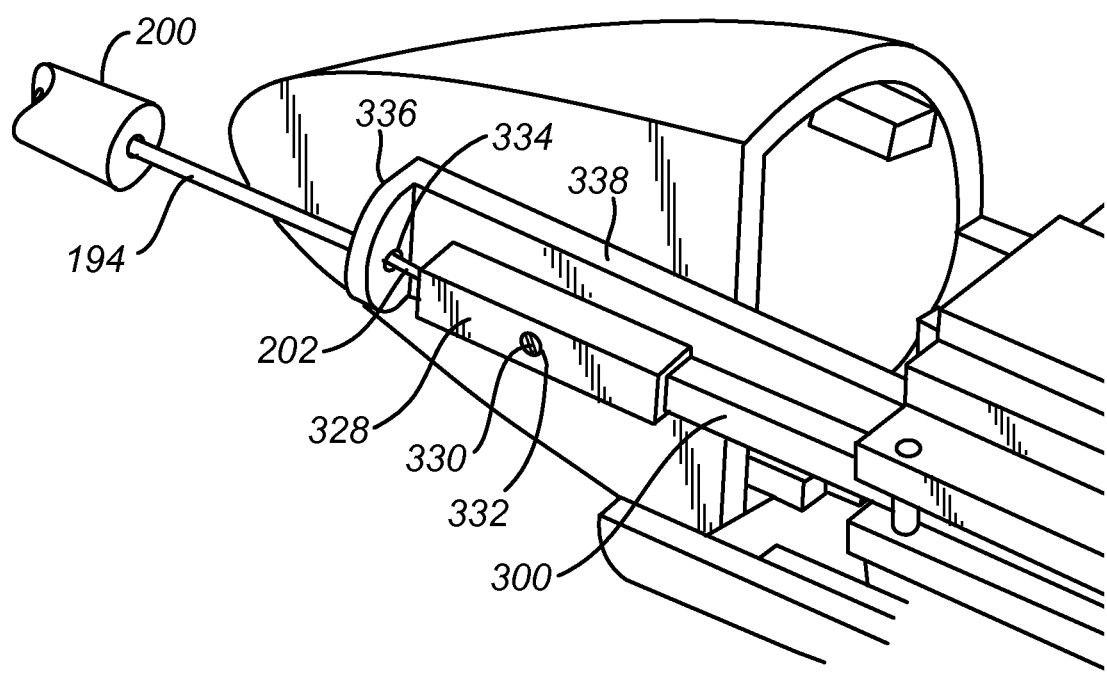
FIG. 24 is a detail view of the portion of FIG. 22 indicated by the area 24-24.

With reference to FIG. 24, a tubular rectangular sleeve 328 receives a proximal end of the pushing member 202 and a distal end of the piston 300. A set screw 330 oriented in the transverse direction passes through a tapped hole 332 into the sleeve 328 and pins the proximal end of the pushing member 202 to the distal end of the piston 300. Alternative configurations for securing the pushing member 202 to the piston 300 could be substituted, such as adhesion with or without the sleeve 328, welding with or without the sleeve 328, etc. Collectively, the powered drive member 280, the bevel gears 320, 322, the axle 278, the flywheel 312, the link rod 306, the piston 300 and the sleeve 328 may comprise another embodiment of a reciprocation drive. The reciprocation drive may, however, include substitute components and/or additional components.

The pushing member 202 passes through an aperture 334 in a transverse plate 336, which is supported at a distal end of an arm 338 extending from the distal base 262. The arm 338 is shaped as a rectangular bar, but could have any shape. The aperture 334 supports the pushing member 202 to resist buckling and/or kinking.

With further reference to FIG. 24, a proximal end of the retractable sheath 194 is secured to a distal side of the transverse plate 336. In one embodiment, the retractable sheath 194 is received in the aperture 334 and bonded thereto, such as with an adhesive, welding, etc. With reference to FIGS. 3 and 4, the stationary sheath 198 is received within a lumen of the nose cone 200, a proximal end of which is secured to a distal face of the fourth housing portion 250 by any suitable means, such as adhesive, welding, etc.

Operation

FIGS. 22, 15-19, 25 and 26 illustrate operation of the device 240 illustrated in FIGS. 20-24. FIGS. 15, 16 and 22 show the device 240 in the ready to use configuration. With reference to FIGS. 15 and 16, a distal portion of the retractable sheath 194 extends from a distal end of the stationary sheath 198. The distal portion of the retractable sheath 194 is disposed within the fallopian tube 220 with the distal end of the stationary sheath 198 positioned at or near the ostium 222. The fork 212 is positioned just inside a distal end of the retractable sheath 194, with the occlusive implant 218 occupying the space around the pushing member 202 and within the retractable sheath 194 lumen.

The fallopian tube 220 may be accessed transcervically, as described above with respect to the previous embodiment. When proper positioning of the sheaths 194, 198 has been verified, the operator activates the device 240. To activate the occlusive implant delivery device 240, the operator activates the powered drive member 280. For example, the device 240 may include an ON/OFF switch (not shown), or any other means of switching the flow of power to the drive member 280. Once powered on, the output shaft 318 of the drive member 280 rotates. With reference to FIG. 22, this rotational motion is transmitted to the flywheel 312 through the bevel gears 320, 322 and the axle 278. Rotational motion of the flywheel 312 induces reciprocal longitudinal motion of the piston 300 through the link rod 306. Reciprocal longitudinal motion of the piston 300 generates reciprocal motion of the pushing member 202.

With reference to FIG. 17, reciprocal longitudinal motion of the pushing member 202 incrementally or segmentally expels the fibrous implant 218 from the retractable sheath 194. Once expelled, the implant 218 can self-expand to fill and occlude the fallopian tube 220. In contrast to the embodiment of FIGS. 3-14, in which the retractable sheath 194 retracts at regular intervals as the second pin 170 of the pawl 150 snaps into successive ratchet teeth 52, in the embodiment of FIGS. 20-24 the retractable sheath 194 retracts in response to back pressure generated by increasing density of the expelled portions of the implant 218. As described above, and with reference to FIGS. 22 and 25, the linear biasing member 148 biases the base 262 in the distal direction. This bias is transmitted to the pushing member 202 and the retractable sheath 194, which is secured to the arm 338 of the base 262 (FIG. 24). As more and more of the implant 218 is expelled from the retractable sheath 194 due to the reciprocating motion of the pushing member 202, back pressure builds on the distal tip of the retractable sheath 194 and/or the pushing member 202, which contact the implant 218. This force is directed proximally, opposite the force imparted on the base 262/retractable sheath 194/pushing member 202 by the linear biasing member 148. As the back pressure increases, it eventually overcomes the distally directed force of the linear biasing member 148, and the base 262/retractable sheath 194/pushing member 202 begin moving proximally as additional portions of the implant 218 are expelled and become packed to a sufficient density, as shown in FIGS. 17-19, 25 and 26.

With reference to FIG. 22, as the base 262 moves proximally with respect to the housing 242, engagement between the planar portion 264 of the base 262 and the side rails 260 guides the longitudinal movement of the base 262 with respect to the housing 242. In particular, the planar portion 264 of the base 262 is located at an elevation below the side rails 260, with the side rails 260 overlapping the planar portion 264. Proximal movement of the base 262 with respect to the housing 242 compresses the linear biasing member 148 (FIG. 26). The linear biasing member 148 is confined between the rails 268, the second surface of the planar portion 264, and the second portion 246 of the housing 242. This confinement resists buckling of the linear biasing member 148.

Employing passive retraction drives, the device 37 of FIGS. 2A-2B and the device 240 of FIGS. 20-24 may advantageously create a desired or substantially uniform packing density for the implant 39/218. As the implant 39/218 is expelled and the retractable sheath 32/194 and pushing member 33/202 retract due to back pressure, the packing force F applied to the implant 39/218 by the distal face of the retractable sheath 32/194 and/or pushing member 33/202 is equal to F=kx, where k is the spring constant of the biasing member 38/148 and x is the displacement of the distal end of the biasing member 38/148 from its equilibrium position. The packing force F applied to the implant 39/218 can thus be kept substantially constant if the ready-to-use configuration of the device 37/240 includes pre-compression in the biasing member 38/148. If the pre-compression is achieved with a relatively large displacement $x_{pre}$ of the distal end of the linear biasing member 38/148, and the additional displacement $x_{add}$ that occurs during placement of the implant 39/218 is relatively small, the change in the magnitude of F, ΔF, during the implantation procedure will be small, where $\Delta F=kx_{pre}-k(x_{pre}+x_{add})$. In the foregoing formula, ΔF will be small where $x_{pre}$ is significantly greater than $x_{add}$.

By achieving a desired or substantially uniform packing density of the implant 39/218 in the HAS, performance of the implant 39/218 can be improved. The implant 39/218 can be made sufficiently dense within the HAS to ensure that the HAS is occluded. At the same time, the implant 39/218 is not made excessively dense, which can make the implant more likely to distend or injure the HAS, or block ingrowth of neighboring tissue into the implant or impede bioabsorption of the implant.

The present embodiments advantageously simplify the delivery of an occlusive implant to a hollow anatomical structure, such as a fallopian tube. For example, the delivery devices don't need to be retracted manually to deploy the implant. When the devices are activated, stored energy or a powered drive member induces movement of the various components. The operator need only position the distal ends of the devices at the treatment site and then commence deployment by, for example, flipping a switch or changing the position of an activation button. The present embodiments thus increase the efficacy of occlusion procedures by reducing the likelihood of operator error.

The above description presents the best mode contemplated for carrying out the present occlusive implant delivery devices and associated methods, and of the manner and process of making and using them, in such full, clear, concise, and exact terms as to enable any person skilled in the art to which it pertains to make and use these devices and methods. These devices and methods are, however, susceptible to modifications and alternate constructions from that discussed above that are fully equivalent. Consequently, these devices and methods are not limited to the particular embodiments disclosed. On the contrary, these devices and methods cover all modifications and alternate constructions coming within the spirit and scope of the devices and methods as generally expressed by the following claims, which particularly point out and distinctly claim the subject matter of the devices and methods.

What is claimed is:

1. A method comprising:
with a delivery system including an outer sheath, an inner sheath slidably received within the outer sheath, an elongate pusher member received within the inner sheath, and an occlusive implant received within the inner sheath; and
longitudinally reciprocating the elongate pusher member within the inner sheath to segmentally expel the occlusive implant from a distal end of the inner sheath, while simultaneously retracting the inner sheath proximally within the outer sheath in response to a back pressure applied at a distal tip of the inner sheath by expelled portions of the occlusive implant.

2. The method of claim 1, further comprising positioning a distal end of the outer sheath at a proximal end of a treatment site prior to beginning the reciprocating of the elongate pusher member.

3. The method of claim 2, further comprising positioning a distal end of the inner sheath at a distal end of the treatment site prior to beginning the reciprocating of the elongate pusher member.

4. The method of claim 2, wherein the treatment site comprises a fallopian tube, and the proximal end of the treatment site comprises an ostium of the fallopian tube.

5. The method of claim 1, wherein retracting the inner sheath comprises retracting in discrete increments.

6. The method of claim 5, wherein each discrete increment corresponds to a defined number of reciprocations of the elongate pusher member.

7. The method of claim 1, wherein the outer sheath remains substantially stationary during the retracting of the inner sheath.

8. The method of claim 7, wherein in an initial configuration the inner sheath extends distally of a distal tip of the outer sheath, so that retracting the inner sheath proximally within the outer sheath causes a distal tip of the inner sheath to approach the distal tip of the outer sheath.

9. The method of claim 1, wherein the inner sheath is biased toward a distal direction.

10. The method of claim 1, wherein a distal tip of the elongate pusher member never extends past a distal tip of the inner sheath while the elongate pusher member reciprocates.

11. The method of claim 1, wherein the delivery system further comprises a reciprocation drive, and the reciprocating and the retracting occur automatically upon activation of the reciprocation drive.

12. The method of claim 1, wherein both of the inner and outer sheaths are sized and configured for transcervical insertion.

13. The method of claim 1, wherein the inner sheath extends distally of a distal tip of the outer sheath, so that retracting the inner sheath proximally within the outer sheath causes a distal tip of the inner sheath to approach the distal tip of the outer sheath.

* * * * *